United States Patent
Ruane et al.

(10) Patent No.: US 7,122,529 B2
(45) Date of Patent: Oct. 17, 2006

(54) COMPOUNDS THAT RELEASE NITRIC OXIDE AT CONTROLLED RATES UPON PHOTOLYSIS

(75) Inventors: Patrick H. Ruane, Baltimore, MD (US); John P. Toscano, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 313 days.

(21) Appl. No.: 10/483,323

(22) PCT Filed: Jul. 12, 2002

(86) PCT No.: PCT/US02/21925

§ 371 (c)(1),
(2), (4) Date: Jan. 12, 2004

(87) PCT Pub. No.: WO03/006427

PCT Pub. Date: Jan. 23, 2003

(65) Prior Publication Data

US 2004/0158048 A1    Aug. 12, 2004

Related U.S. Application Data

(60) Provisional application No. 60/304,413, filed on Jul. 12, 2001.

(51) Int. Cl.
*C07C 291/08*    (2006.01)
*A61K 31/655*    (2006.01)
*A61P 7/00*    (2006.01)

(52) U.S. Cl. .................. 514/149; 534/551; 534/552; 534/556; 534/567; 534/568; 423/405

(58) Field of Classification Search ............... 534/551, 534/552, 556, 567, 568; 514/149; 423/405
See application file for complete search history.

(56) References Cited

U.S. PATENT DOCUMENTS 5,366,997 A * 11/1994 Keefer et al. ............... 514/611
5,374,710 A * 12/1994 Tsien et al. ................ 534/552
5,683,668 A * 11/1997 Hrabie et al. .............. 423/405
5,814,666 A *  9/1998 Green et al. ............... 514/611

FOREIGN PATENT DOCUMENTS

WO        WO 94/27957        12/1994

OTHER PUBLICATIONS

A. Srinivasan et al; Chemistry of the Diazeniumdiolates. 3. Photoreactivity; J. Am. Chem. Soc., 2001, No. 123, pp. 5464-5472.
J. Saavedra et al; Targeting Nitric Oxide (NO) Delivery in Vivo. Design of a Liver-Selective NO Donor . . . ; J. Med. Chem., 1997, No. 40; pp. 1947-1954.
P. Ruane et al; Controlled Photochemical Release of Nitric Oxide from O2-Benzyl-Substituted Diazenlumdiolates; J. Am. Chem. Soc. 2002, No. 124, pp. 9806-9811.

* cited by examiner

*Primary Examiner*—Fiona T. Powers
(74) *Attorney, Agent, or Firm*—Whitham, Curtis, Christofferson & Cook, PC

(57) ABSTRACT

Chemical compounds which release nitric oxide in a controlled manner upon photolysis with light are provided. These compounds are $O^2$-benzyl, $O^2$-naphthylmethyl and $O^2$-naphthylallyl substituted diazeniumdiolates. Also provided are methods of preparing these novel compounds in high chemical yields as well as methods of using these compounds.

11 Claims, 6 Drawing Sheets

COMPOUNDS THAT RELEASE NITRIC OXIDE AT CONTROLLED RATES UPON PHOTOLYSIS

RELATED U.S. APPLICATION DATA

This application claims priority from U.S. Provisional Application 60/304,413 filed on Jul. 12, 2001.

SUPPORT

The U.S. Government has a paid-up license in this invention and the right in limited circumstances to require the patent owner to license others on reasonable terms as provided for by the terms of Contract No. GM 58109-04 awarded by National Institutes of Health.

Support was also received from the American Cancer Society, and a Camille Dreyfus Teacher-Scholar Award, Camille and Henry Dreyfus Foundation.

BACKGROUND

The present invention relates generally to the fields of organic chemistry, biochemistry and/or biological treatment systems. In particular, the present invention is directed to compounds that are capable of releasing nitric oxide (NO) in a controlled manner, as well as methods for the preparation and use thereof.

Nitric oxide has been implicated in a variety of important bioregulatory processes, including neurotransmission, anti-coagulation and vasodilation. In addition, NO is an effector molecule released by macrophages and other cells after immunological activation.

NO is synthesized from the amino acid L-arginine by an enzyme, NO synthase. It is believed that there are at least two forms of the enzyme: a constitutive form which releases NO for short periods in response to receptor or physical stimulation, and a second form which is induced after activation of macrophages, endothelial cells and certain other cells by cytokines and which, once expressed, synthesizes NO for extended periods.

The constitutive form of NO synthase is implicated in the transduction mechanism for soluble guanylate cyclase, and thus is involved in one of the mechanisms whereby cells regulate their own function or communicate with others. In addition, the release of NO in the cardiovascular system acts as a general adaptive mechanism whereby the vascular endothelium responds to changes in its environment and regulates blood flow and blood pressure through action on vascular smooth muscle. NO also regulates the interaction between the endothelium and the platelets; it may also play a role in the control of vascular smooth muscle proliferation. The NO released by the constitutive enzyme may also play regulatory roles in other cells; for example, it is known to be linked to the stimulation by the excitatory amino acids of specific receptors in the central nervous system, and it may participate in regulation of the secretion or action of various hormones.

NO released after immunological stimulation by the other form of the enzyme as part of the host defense mechanism has been shown to be cytotoxic or cytostatic for tumor cells and invasive organisms. Further, some forms of local or systemic tissue damage associated with immunological conditions could prove to be related as well to the release of NO. NO may also play a role in the normal regulation of the response of cells to mitogens, or contribute to the cytotoxic actions of other cells that play a role in specific immunity.

NO is itself extremely poisonous and reactive in the presence of oxygen. It is a highly reactive gas in its pure form, attacking metals and plastics, and can only be obtained in relatively low pressure cylinders. Moreover, NO has limited solubility in aqueous media, making it difficult to introduce reliably into most biological systems without premature decomposition.

In view of the central importance of NO as both a transducer and as an effector molecule, however, it is apparent that agents for the controlled release of NO would be invaluable in the ongoing research on the roles of NO in human physiology and pathology. Moreover, the therapeutic potential of agents that may be employed to release NO in a controlled manner is enormous.

Various vasodilators are known which release NO either spontaneously or upon activation by chemical or enzymatic means. For example, the release of NO from molsidomine (N-ethoxycarbonyl-3-morpholinosydnonimine) begins with an enzymatic hydrolysis catalyzed mainly by liver esterases, followed by a pH-dependent ring opening reaction catalyzed by hydroxyl ions; a subsequent oxidative process is then essential for further decomposition and NO release [Bohn, H. and K. Schoenafinger, "Oxygen and Oxidation Promote the Release of Nitric Oxide from Sydnonimines," J. Cardiovasc. Pharmacol. 14 (Suppl.11):S6-S12 (1989)]. The vasodilators glyceryl trinitrate and sodium nitroprusside release nitric oxide upon redox activation. Other agents, such as iron-sulfur cluster nitrosyls, decompose spontaneously to release NO [Flitney, F. W. et al., "Selective retention of iron-sulphur cluster nitrosyls in endothelial cells of rat isolated tail artery: association with protracted vasodilator responses, J. Physiol. 459:89P (1993)].

One example of a compound that spontaneously releases NO is a class of diazeniumdiolate compounds. Anions such as 1-(N,N-dialkylamino)diazen-1-ium-1,2-diolates (see compound 1 (X=NR$_2$, R=alkyl)) are stable as solid salts, but release up to two moles of NO when dissolved in aqueous solution at physiologically relevant conditions. Compound 1 is shown below in its anionic form. Compound 1 appears in this state throughout the description, the sodium ion is not shown. Keefer et al. have shown that the rate of NO release from diazeniumdiolates is dependent on the nature of the organic anion (X$^-$), and have developed diazeniumdiolate compounds with half-lives of between 1.8 seconds to 56 hours in aqueous buffer at a pH of 7.4 at 37° C. Maragos, C. M.; Morley, D.; Wink, D. A.; Dunams, T. M.; Saavedra, J. E.; Hoffman, A.; Bove, A. A.; Isaac, L.; Hrabie, J. A.; Keefer, L. K. *J. Med. Chem.* 1991, 34, 3242–3247. (b) Keefer, L. K.; Nims, R. W.; Davies, K. M.; Wink, D. A. *Methods in Enzymology* 1996, 268, 281–293.

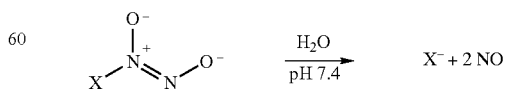

1

X = NR$_2$, R = alkyl

Diazeniumdiolates have shown great potential in a variety of medical applications requiring the rapid production (e.g., to produce a fast, but transient drop in blood pressure) or gradual release of NO (e.g., to study the effects of prolonged cytostasis on vascular smooth muscle cells).

One such strategy proposes to deliver NO to a specific site by anchoring diazeniumdiolate in polymeric matrices, restricting the release of NO to only those cells to which the polymer is in physical contact. Another strategy proposes using pro-drug derivatives that are unable to release NO until they have been metabolically converted to diazeniumdiolate by enzymes specific to the target cell type. For example, diazeniumdiolates masked by $O^2$-alkylation were shown to protect the liver in rats from cell death while minimally affecting systemic blood pressure, after being selectively dealkylated by oxidative enzymes specifically found in the liver.

It is therefore an object of the present invention to provide compositions for controlled delivery of nitric oxide that remain stable until it is desired to release NO by a particular triggering means, as well as towards methods for the preparation and uses thereof.

A wide variety of groups labile to photolysis referred to as "caging" structures are known in the art. The commonly employed 2-nitrobenzyl photosensitive protecting group has been used to develop potential photochemical precursors (compound 2, R=H, $OCH_3$, $OCH_2CO_2Et$) to diazeniumdiolates. These compounds of Makings and Tsien are described in U.S. Pat. No. 5,374,710 and have the general formula:

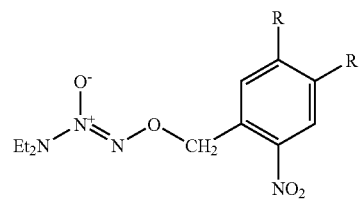

Photolysis of compound 2 results in poor yields of NO with correspondingly low quantum yields. Nonetheless, these phototriggered NO donors were used to inhibit thrombin-stimulated platelet aggregation, to study the induction of long-term depression in the cerebellum and to examine long-term potentiation in culture of hippocampal neurons.

However, in the literature, it has been determined that when photolyzed, simple $O^2$-substituted diazeniumdiolates (such as compound 2) have been found to breakdown by at least two primary pathways upon exposure to light [Srinivasan, A.; Kebede, N.; Saavedra, J. E.; Nikolaitchik, A. V.; Brady, D. A.; Yourd E.; Davies, K. M.; Keefer, L. K. and Toscano, J. P. *J. Am. Chem. Soc.* 2001 123, 5465–5472]. As shown in the reaction pathway below (scheme 1) (and as further described in Example 9 below), the major breakdown pathway of the diazeniumdiolate compounds of Makings and Tsien, involves the formation of potentially carcinogenic nitrosamine ($R_2NN=O$) (compound 12) and a reactive oxygen-substituted nitrene (RON) (compound 13) as by-products (Path A) (shown in scheme 1 below). Minor amounts of NO, potentially produced by secondary photolysis of the nitrosamine are observed. Due to the toxic nature of these breakdown products, pharmaceuticals based on such diazeniumdiolate derivatives should be avoided.

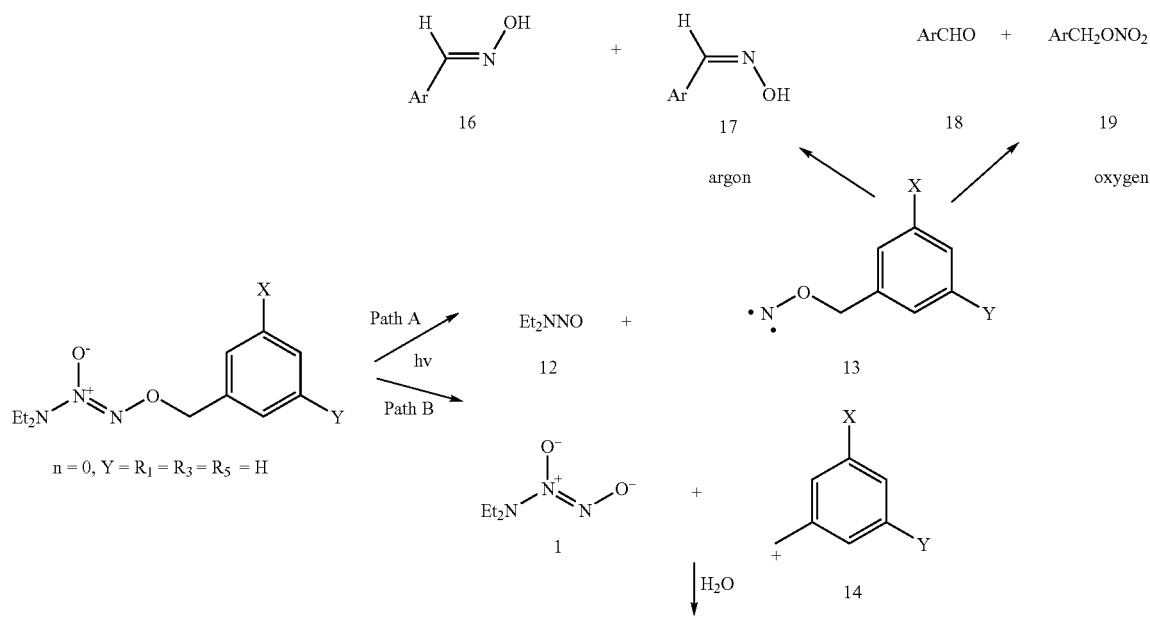

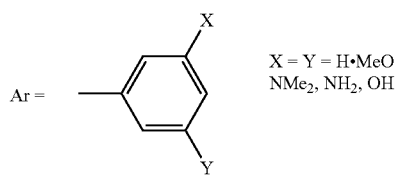
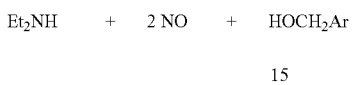

It is one aspect of this invention to avoid the production of toxic byproducts produced by Path A. The prevention of toxic by-products may be achieved by choosing alternate caging structures that help favor the formation of non-toxic by-products upon photolysis.

SUMMARY OF THE INVENTION

This invention relates to novel photochemical precursors of NO. The invention provides novel $O^2$-substituted diazeniumdiolate compounds that are capable of releasing NO at a controlled rate upon being triggered by light. The novel compounds may comprise any one of the following structures:

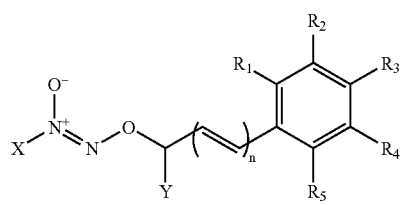

3

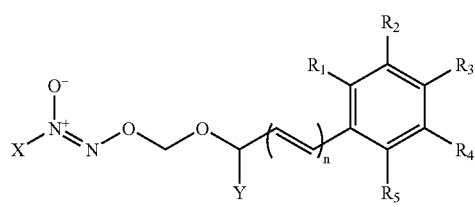

4

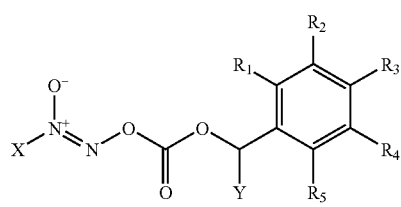

5

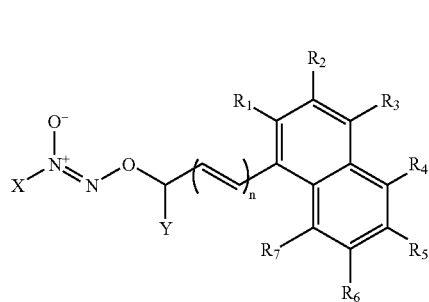

6

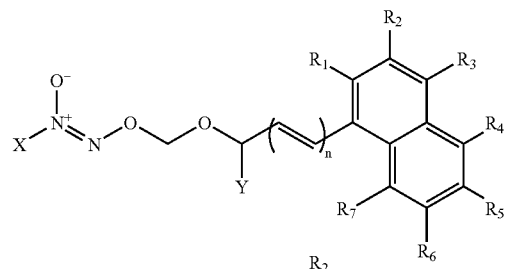

7

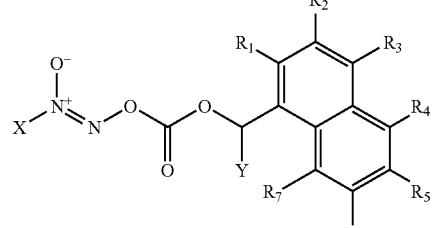

8

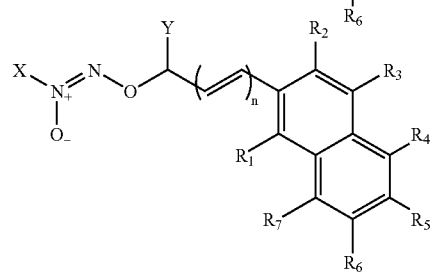

9

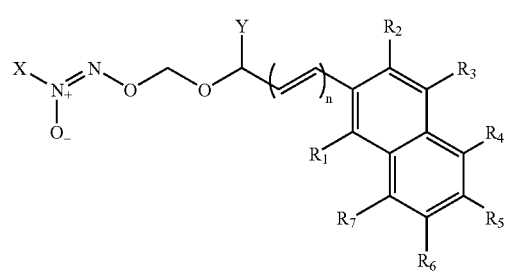

10

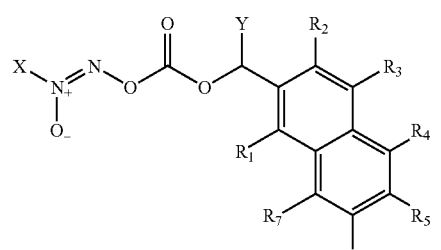

11 n = 0, 1 wherein:

X=—NR¹R², where R¹ and R² are selected from the group consisting of —H, —C₁ through —C₁₂ alkyl, phenyl, substituted phenyl, —R'NH₂, and —R'—NH—R", where R' and R" are alkyl groups including straight chain and branched groups, as well as cycloalkcyl, and where X may also equal prolinyl, imidizoyl, pyrrolyl, or pyridyl, where these groups are bonded at N;

Y=—H, —C₁ through —C₁₂ alkyl, phenyl, substituted phenyl, —OR', or —NR'R", where R' and R" are alkyl groups including straight chain and branched groups, as well as cycloalkyl; and R₁–R₇=—H, —C₁ through —C₁₂ alkyl, phenyl, substituted phenyl, —OH, —OR', —O(CH₂CH₂O)ₙH, where n=1–12, —NH₂, —NR'R", —SH, —SR', —R'CO₂H, —R'CO₂R", —OR'CO₂H, or —OR'CO₂R", where R' and R" are alkyl groups including straight chain and branched groups, as well as cycloalkyl, and where R₁–R₇ may also equal any sugar or carbohydrate where this group is bonded at O.

Also disclosed are methods of producing such compounds 3–11 in high chemical yield.

For pharmaceuticals and other uses, it would be particularly advantageous if the release of NO from diazeniumdiolate compounds could be controlled such that once the molecule is targeted to a particular location, the compound could be triggered to release NO by an external stimulus such as pH or light or temperature.

It is therefore an object of the present invention to provide compositions for controlled delivery of nitric oxide that remain stable until it is desired to release NO at a well defined and reproducible rate by a particular triggering means, as well as towards methods for the preparation and uses thereof.

A method of using these compounds in a procedure to inactivate pathogens in blood or other fluids is further contemplated by this invention.

DETAILED DESCRIPTION

Figure 1:
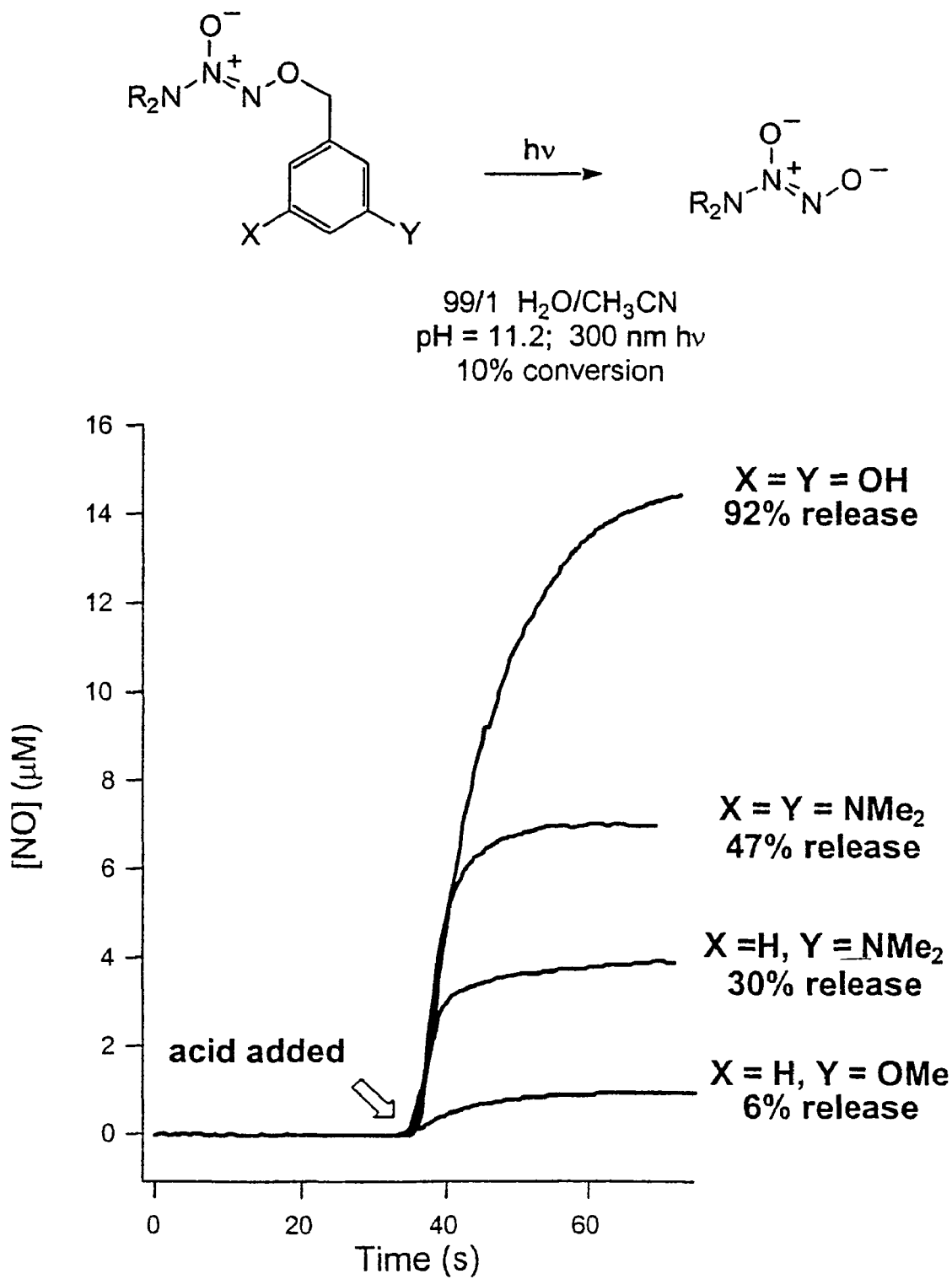
FIG. 1 is a graph which shows the amount of nitric oxide produced upon photolysis from a selection of meta substituted benzyl derivatives having a backbone of compound 3.

This invention is directed toward novel photosensitive precursors which may also be referred to as "caged compounds" or "phototriggers" to diazeniumdiolate anions, which release NO in a temporally controlled manner.

These photochemical precursors are unique in that they can deliver NO specifically to a targeted site in a temporally controlled manner. The specificity of NO delivery is controlled by photolysis of an appropriate photoprotecting group such as a substituted benzyl, 1- or 2-methylnapthyl or substituted 1- or 2-naphthylallyl group. The temporal aspects of NO release are controlled by the substituent X of compounds 3–11, which determines the ultimate rate of NO release from the uncaged diazeniumdiolate. These compounds may be photolyzed at wavelengths between 254–700 nm. Most preferred for use in this invention are wavelengths at the higher end of the light spectrum. Higher wavelengths are less toxic to biological systems and provide greater penetration through cellular membranes than lower wavelengths.

Definitions

For purposes of the present invention, a photosensitive compound means a compound that undergoes reaction upon irradiation with light, typically with wavelengths in the ultraviolet and/or visible region of the spectrum.

An NO-releasing compound means a compound that is capable of releasing NO upon a stimulus by a temperature change, a pH change, or exposure to light.

EXAMPLES

A series of O²-substituted diazeniumdiolates, including O²-benzyl, O²-naphthylmethyl and O²-naphthylallyl substituted diazeniumdiolates were prepared and the effect of electron donating substituents on the photochemistry and efficiency of NO release after photolysis was studied.

Unless otherwise noted, materials were obtained from Aldrich Chemical Co. and used without further purification. Acetonitrile and dichloromethane were distilled from calcium hydride and tetrahydrofuran was distilled from sodium/benzophenone before use. N,N-dimethylformamide (DMF) was dried by azeotropic distillation with benzene and then further distilled over neutral alumina under vacuum. Melting points were determined on a Melt Temp II apparatus and are uncorrected. Infrared spectra were recorded on a Bruker IFS 55 Fourier transform IR at 4 cm⁻¹ resolution. ¹H NMR and ¹³C NMR spectra were recorded on a Bruker AMX 300 (300 MHz) or a Varian Unity Plus 400 (400 MHz) Fourier transform NMR spectrometer. Resonances are reported in δ units downfield from tetramethylsilane. Mass spectra were collected with a VG 70-S mass spectrometer in the fast atom bombardment mode with sample introduction via direct probe. HPLC analysis was performed on a Waters Delta 600 System equipped with a Model 6000A pump, a Model 2487 dual wavelength UV detector, and a Model U6K injector with a 20 µL injector loop (Rhedyne). A Waters C-18 Symmetry analytical column (3.9×150 mm) was used. Absorption spectra were obtained using a Hewlett Packard 8453 diode array spectrophotometer.

Example 1

This example describes the general procedure for coupling sodium-1-(N,N-diethylamino)-diazen-1-ium-1,2-diolate (compound 1, shown below) with a benzyl bromide protecting group.

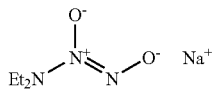

A slurry of 0.39 g (2.52 mmol) diazeniumdiolate compound 1, prepared in 10 mL dry tetrahydrofuran and cooled to −78° C. To this mixture was added one equivalent of the appropriate benzyl bromide (prepared by literature methods) in 2 mL DMF via cannula. The reaction mixture was stirred under an inert atmosphere and allowed to warm to room temperature over 24 hours. Diethyl ether (20 mL) was then added; the sodium bromide was removed by gravity filtration, diethyl ether and tetrahydrofuran were removed by rotary evaporation, and DMF was removed under vacuum. The resulting yellow oil was dissolved in dichloromethane and washed with water. The organic layer was dried over magnesium sulfate and concentrated by rotary evaporation to yield the desired product which was purified on a silica column using dichloromethane as the eluent.

Example 2

This example describes the characteristics of $O^2$-(3-methoxybenzyl)-1-(N,N-diethylamino)-diazen-1-ium-1,2-diolate (having the backbone of compound 3, where n=0, Y=H, $R_1=R_3=R_4=R_5$=H, $R_2$=MeO, X=diethylamino).

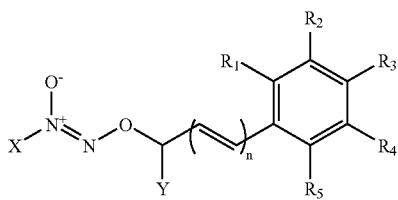

80% yield as a yellow oil, $^1$H NMR (300 MHz, CDCl$_3$), δ 1.05 (t, 6H, J=8 Hz), 3.07 (q, 4H, J=8 Hz), 3.82 (s, 3H), 5.25 (s, 2H), 6.86–6.88 (d, 1H, J=8.5 Hz), 6.93–6.99 (m, 2H), 7.23–7.28 (m, 1H); $^{13}$C NMR (400 MHz, CDCl$_3$) δ 11.64, 48.89, 55.39, 75.71, 113.62, 114.56, 128.81, 129.71, 137.38, 159.86; MS (FAB) m/z (rel. inten.) 276 (M+Na, 100), 254 (M+H, 3); UV-Vis (CH$_3$CN) $\lambda_{max}$ 273 nm (ε=3555 M$^{-1}$ cm$^{-1}$).

Example 3

This example describes the characteristics of $O^2$-(3,5-dimethoxybenzyl)-1-(N,N-diethylamino)-diazen-1-ium-1,2-diolate (having the backbone of compound 3, where n=0, Y=H, $R_1=R_3=R_5$=H, $R_2=R_4$=MeO, X=diethylamino)

90% yield as a yellow oil, $^1$H NMR (300 MHz, CDCl$_3$) δ 1.05 (t, 6H, J=7 Hz), 3.05 (q, 4H, J=7 Hz), 3.80 (s, 6H), 5.27 (s, 2H), 6.41 (t, 1H), 6.53 (d, 2H).

Example 4

This example describes the preparation of $O^2$-(3-dimethylaminobenzyl) and $O^2$-(3,5-bisdimethylaminobenzyl)-1-(N,N-diethylamino)-diazen-1-ium-1,2-diolate (having the backbone of compound 3, where n=0, Y=H, $R_1=R_3=R_4=R_5$=H, $R_2$=NMe$_2$, X=diethylamino) and compound 3, where n=0, Y=H, $R_1=R_3=R_5$=H, $R_2=R_4$=NMe$_2$, X=diethylamino).

The methyl esters of the commercially available 3-amino and 3,5-diaminobenzoic acids were prepared according to literature procedures. Each amino group was then methylated to the corresponding trimethylammonium salt using a five fold excess of methyl iodide. Reduction of the ammonium salts with a large excess of lithium aluminum hydride gave the desired 3-dimethyl amino and 3,5-bis dimethyl amino benzyl alcohols respectively in 80% yield. The bromide precursors were prepared by reacting the corresponding benzyl alcohols with bromide ion. These bromides were too reactive to be isolated and were coupled immediately with diazeniumdiolate compound 1 to afford the two compounds in yields of ca. 20%.

Example 5

This example describes the characteristics of $O^2$-(3-dimethylaminobenzyl)-1-(N,N-diethylamino)-diazen-1-ium-1,2-diolate (having the backbone of compound 3, where n=0, Y=H, $R_1=R_3=R_4=R_5$=H, $R_2$=NMe$_2$, X=diethylamino).

30% yield as a yellow oil, $^1$H NMR (300 MHz, CDCl$_3$) δ 1.07 (t, 6H, J=8 Hz), 2.97 (s, 6H), 3.06 (q, 4H, J=8 Hz), 5.24 (s, 2H), 6.67–6.75 (m, 3H), 7.18–7.26 (m, 1H); $^{13}$C NMR (400 MHz, CDCl$_3$) δ 11.6, 40.69, 48.86, 76.4, 112.46, 112.82, 116.73, 129.28, 136.61, 150.85; MS (FAB) m/z (rel. inten.) 289 (M+Na, 100), 265 (M−H, 5); UV-Vis (CH$_3$CN) $\lambda_{max}$ 306 nm (ε=3058 M$^{-1}$cm$^{-1}$).

Example 6

This example describes the characteristics of $O^2$-(3,5-bis-dimethylaminobenzyl)-1-(N,N-diethylamino)-diazen-1-ium-1,2-diolate (having the backbone of compound 3, where n=0, Y=H, $R_1=R_3=R_5$=H, $R_2=R_4$=NMe$_2$, X=diethylamino).

20% yield as a yellow oil, $^1$H NMR (300 MHz, CDCl$_3$) δ 1.05 (t, 6H, J=8 Hz), 2.96 (s, 12H), 3.07 (q, 4H, J=8 Hz), 5.20 (s, 2H), 6.02–6.03 (s, 1H), 6.19–6.20 (s, 2H); $^{13}$C NMR (400 MHz, CDCl$_3$) δ 11.81, 41.03, 48.95, 77.235, 97.78, 102.53, 137.24, 152.01; MS (FAB) m/z (rel. inten.) 332 (M+Na, 82), 309 (M+, 20); UV-Vis (CH$_3$CN) $\lambda_{max}$ 317 nm (ε=3704 M$^{-1}$cm$^{-1}$).

Example 7

This example describes the preparation and characteristics of $O^2$-(3,5-dihydroxybenzyl)-1-(N,N-diethylamino)-diazen-1-ium-1,2-diolate (having the backbone of compound 3, where n=0, Y=H, $R_1=R_3=R_5$=H, $R_2=R_4$=OH, X=diethylamino).

The commercially available 3,5-dihydroxybenzoic acid was esterified in quantitative yield to afford the corresponding methyl ester. The phenolic hydroxy groups were converted to methoxymethyloxy functionalities. Lithium aluminum hydride reduction gave the alcohol which was brominated under non-acidic conditions. The bromide was coupled with compound 1 as described above in high yield and the methoxymethyloxy groups were removed using aqueous acid to afford compound 3, n=0, Y=H, $R_1=R_3=R_5$=H, $R_2=R_4$=OH in quantitative yield. $^1$H NMR (300 MHz, CDCl$_3$), δ 1.15 (s, 6H, J=7 Hz), 3.09 (q, 4H, J=7 Hz), 5.12 (s, 2H), 6.30 (t, 1H, J=2 Hz), 6.44 (d, 2H, J=2 Hz), 6.80 (s br, 2H).

Example 8

Analysis of the above described organic products produced following photolysis of the compounds was studied in argon and oxygen-saturated 90%–99% aqueous acetonitrile. Quantification of NO released upon photolysis was performed electrochemically with an inNO Nitric Oxide Measuring System using an amiNO-2000 probe (Innovative Instruments Inc., Tampa, Fla.). The amiNO-2000 probe was calibrated using ascorbic acid/sodium nitrite before and after NO measurements were conducted. In order to differentiate NO production arising from diazeniumdiolate from non-diazeniumdiolate derived NO, the dependence of diazeniumdiolate decomposition rate on pH was utilized. At room temperature, sodium-1-(N,N-diethylamino)-diazen-1-ium-1,2-diolate compound 1, has a lifespan of several hours at pH 11, but only several seconds at a pH of 3. Aqueous solutions at pH 11 of the compounds were irradiated and then analyzed for NO. Any NO detected under these conditions must arise from a non-diazeniumdiolate pathway. For all compounds examined the amount of NO formed from such a pathway was negligible. To liberate NO associated with the photoreleased diazeniumdiolate, solutions were acidified with 1.0 M $H_2SO_4$ to a pH of between 2–3. In each case, the yield of NO was determined from a series of measurements following photolysis to a range of percent conversions. NO yields were found to be linear for up to 20–40% conversion. NO yields determined from these experiment along with the observation that compound 1 dissociates to give 1.5 equivalents of NO were used to derive yields of photoreleased diazeniumdiolates from the compounds studied.

Determination of the absolute amount of NO released from the thermal decomposition of sodium-1-(N,N-diethylamino)-diazen-1-ium-1,2-diolate compound 1, and sodium-1-(piperidin-1-yl)-diazen-1-ium-1,2-diolate compound 20.

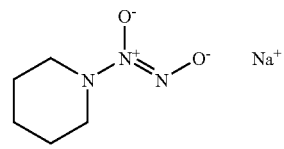

20

Stock solutions of both compounds 1 and 20 were prepared to be 100 μM in aqueous solution at pH=12.2. A series of μL aliquots of the stock solution were diluted into 3 mL of aqueous solution at pH=12.2 resulting in an array of concentrations from 0.15–0.66 μM. The probe was allowed to equilibrate in the sample solutions before the addition of 10 μL of 1.0 M sulfuric acid. The final concentration of NO in solution after complete decomposition was determined by the calibration curve, and a linear plot of NO released vs. initial concentration was obtained. By this method it was determined that compounds 1 and 20 release 1.5 and 1.8 eq. of NO respectively.

TABLE 1

Quantum yields and diazeniumdiolate release from compounds 2 and 3.

| Reactant<br>n = 0, Y = H, $R_1$ = $R_3$ = $R_5$ = H,<br>X = $NEt_2$ | Solvent %<br>$H_2O/CH_3CN$ | Photolysis<br>λ (nm) | Quantum<br>Yield[a] | %<br>Diazeniumdiolate[b] |
|---|---|---|---|---|
| 2 (R = H) | 99/1 | 300 | c | 5 |
| 2 (R = OMe) | 99/1 | 300 | c | 3 |
| 3 ($R_2$ = $R_4$ = H) | 99/1 | 300 | c | trace |
| 3 ($R_2$ = MeO, $R_4$ = H) | 99/1 | 300 | c | 6 |
| 3 ($R_2$ = $R_4$ = MeO) | 99/1 | 300 | c | 10 |
| | 99/1 | 254 | 0.17 | c |
| | 0/100 | 254 | 0.35 | c |
| 3 ($R_2$ = $NMe_2$, $R_4$ = H) | 99/1 | 300 | 0.04 | 35 |
| | 0/100 | 300 | 0.17 | c |
| | 99/1 | 254 | 0.25 | c |
| | 0/100 | 254 | 0.60 | c |
| 3 ($R_2$ = $R_4$ = $NMe_2$) | 99/1 | 300 | 0.05 | 47 |
| | 0/100 | 300 | 0.18 | c |
| | 99/1 | 254 | 0.26 | c |
| | 0/100 | 254 | 0.53 | c |
| 3 ($R_2$ = $R_4$ = OH) | 99/1 | 300 | 0.87 | 92[d] |

[a]Determined with the potassium ferrioxalate, 1,3-cycloheptadiene, or Reinecke's Salt actinometer.
[b]Based on percent reactant converted (determined by HPLC analysis), the yield of NO measured and the observation that diazeniumdiolate 1 gives 1.5 equivalents of NO. Estimated error = ±5%.
[c]Not determined.
[d]Photolysis at pH 11.2

Example 9

The results of the photochemistry of the above described $O^2$-substituted diazeniumdiolates (compounds 3) are interpreted below in Scheme 1 as Path A (undesired) and Path B (desired).

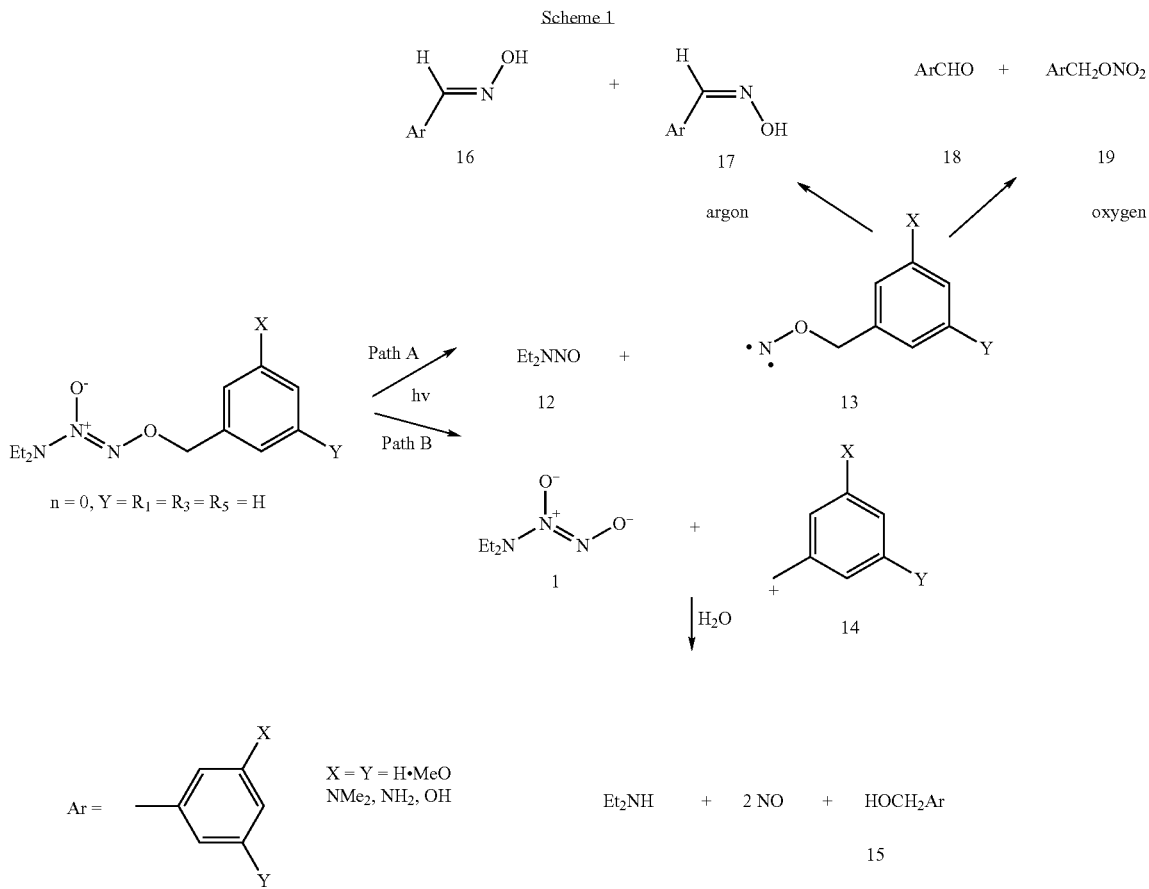

Path A involves the production of carcinogenic nitrosamine (compound 12) and oxynitrene (compound 13). The oxynitrene either rearranges to an intermediate C-nitroso compound that forms oximes (compounds 16, 17) or is trapped by oxygen to produce aldehyde (compound 18) and HONO and nitrate (compound 19).

Path B involves the formation of ionic products diazeniumdiolate (compound 1) and benzyl cation (compound 14). In the solvent water, compound 14 is trapped to provide benzyl alcohol (compound 15) and diazeniumdiolate (compound 1) dissociates to produce diethylamine and NO.

As can be seen from Example 8, the relative contributions of Path A and Path B is strongly dependant on the substitution pattern of the aromatic ring. The yield of nitrosamine (compound 12) decreases and NO and alcohol (compound 15) increases with stronger π-donating meta substituents.

Example 10

Since Path B is favored with the addition of strong π-donating meta substituents, the dihydroxybenzyl derivative of compound 3, n=0, Y=H, $R_1=R_3=R_5=H$, $R_2=R_4=OH$ ($O^2$-3,5-dihydroxybenzyl substituted diazeniumdiolate) was studied in further detail. Consistent with the expected large effect of oxyanionic meta substitution, when compound 3, n=0, Y=H, $R_1=R_3=R_5=H$, $R_2=R_4=OH$ is irradiated (Rayonet, 300 nm) in an aqueous solution of pH 11.2 (containing 1% acetonitrile) to 5–35% conversion, the amount of NO detected corresponded to a yield of photoreleased diazeniumdiolate compound 1 of approximately 92%. A comparison of selected results observed with $O^2$-substituted diazeniumdiolate derivatives having the backbone of compound 3 is shown in FIG. 1. After photolysis of the compound (t=0 sec) there is no nitric oxide production. NO is only liberated upon acidification of the solution (t=35 sec) indicating that all the nitric oxide is derived from the photochemically liberated diazeniumdiolate compound 1.

Example 11

In order to extend the useful range of photolysis wavelengths to above 330 nm, the following series of $O^2$-naphthylmethyl and $O^2$-naphthylallyl substituted diazeniumdiolates compounds 6, 9, were prepared. The effect of electron-donating substituents on the observed photochemistry and on the efficiency of NO release was studied.

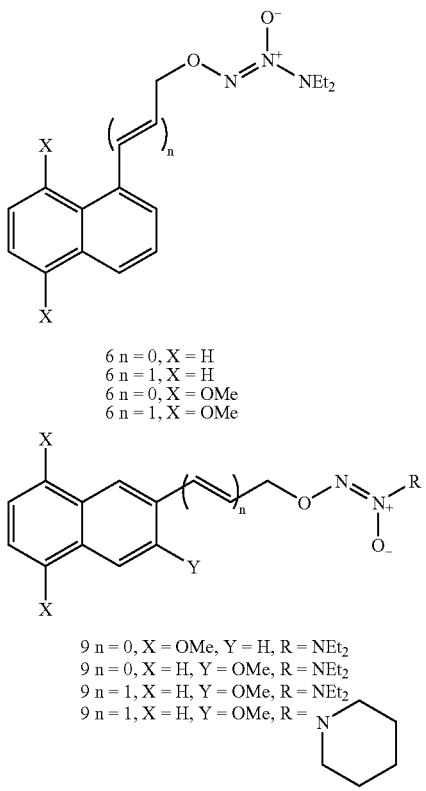

Figure 2A:
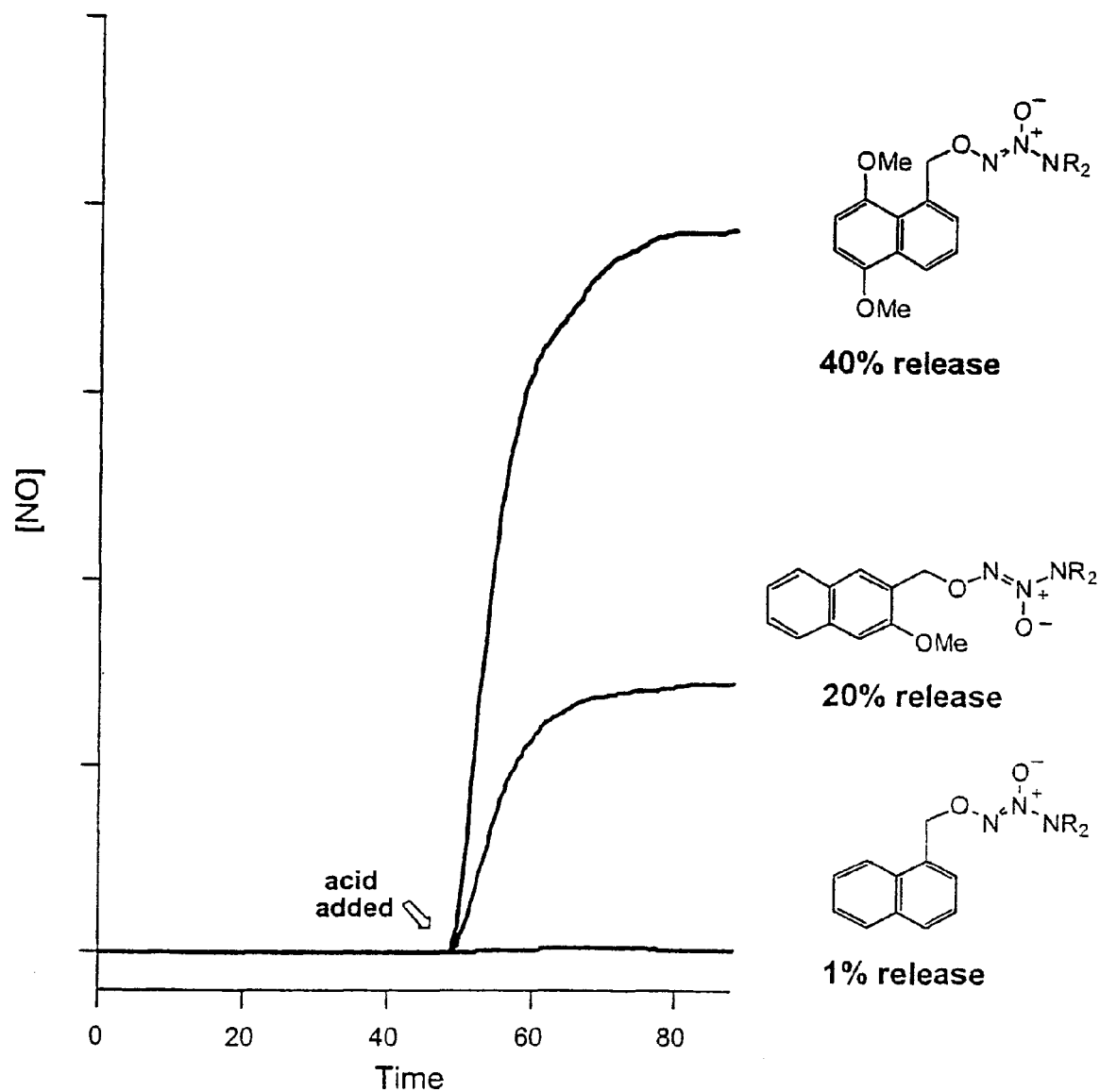
FIGS. 2a and 2b are graphs depicting the amount of nitric oxide produced upon photolysis from a selection of 1- and 2-methylnaphthyl and 1-and 2-allylnaphthyl-O²-substituted diazeniumdiolates having a backbone of compounds 6 and 9.
Figure 2B:
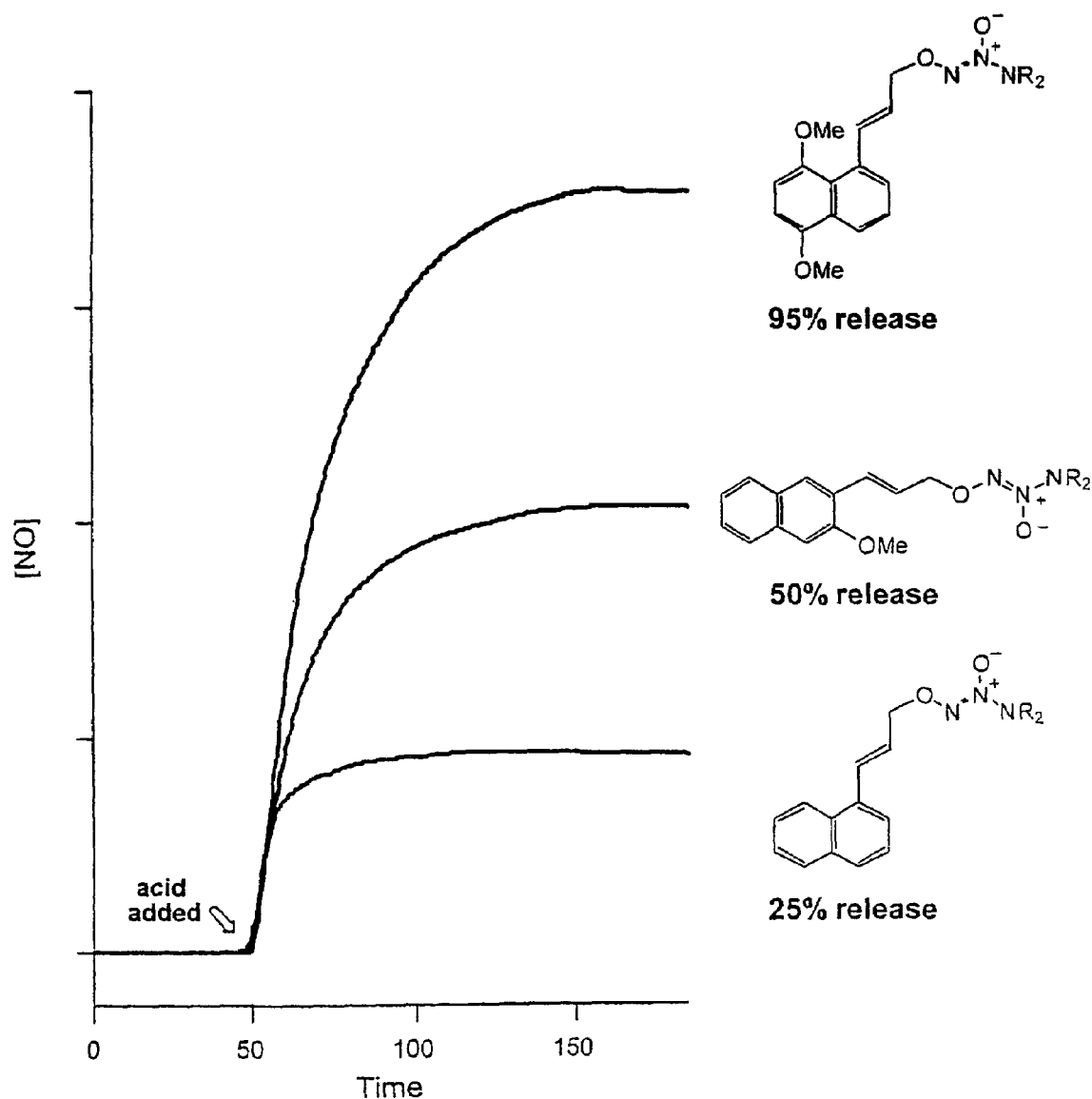

6 n = 0, X = H
6 n = 1, X = H
6 n = 0, X = OMe
6 n = 1, X = OMe 9 n = 0, X = OMe, Y = H, R = NEt$_2$
9 n = 0, X = H, Y = OMe, R = NEt$_2$
9 n = 1, X = H, Y = OMe, R = NEt$_2$
9 n = 1, X = H, Y = OMe, R = piperidinyl FIGS. 2a and 2b show the amount of nitric oxide production from a selection of 1- and 2-methylnaphthyl and 1- and 2-allylnaphthyl-O$^2$-substituted diazeniumdiolates compound 6 and compound 9. After photolysis (t=0 sec) there is no nitric oxide production, it is only liberated upon acidification of the solution (t=50 sec) indicating that all the nitric oxide is derived from the photochemically liberated diazeniumdiolate compound 1.

Example 12

This example describes the general procedure for coupling 1-(N,N-diethylamino)-diazen-1-ium-1,2-diolate (compound 1 shown below) and 1-(piperidin-1-yl)-diazen-1-ium-1,2-diolate (compound 20 shown below) with the corresponding bromide to produce the above compounds 6 and 9.

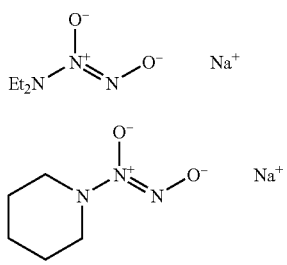

A slurry of (2.52 mmol) diazeniumdiolate in 10 mL dry tetrahydrofuran was cooled to −78° C. To this mixture was added one equivalent of the appropriate bromide in 2 mL dry DMF via cannula. The reaction mixture was stirred under an inert atmosphere and allowed to warm to room temperature over 24 hours. Diethyl ether (20 mL) was added; the sodium bromide was removed by gravity filtration, diethyl ether and tetrahydrofuran were removed by rotary evaporation, and DMF was removed under vacuum. The resulting yellow oil was dissolved in dichloromethane and washed with water. The organic layer was dried over magnesium sulfate and concentrated by rotary evaporation to yield the desired product, which was purified on a silica column using dichloromethane as the eluent.

Example 13

This example describes the characteristics of O$^2$-(1-naphthylmethyl)-1-(N,N-diethylamino)-1-diazen-1-ium-1,2-diolate (having the backbone of compound 6, where n=0, Y=H, R$_1$–R$_7$=H, X=diethylamino).

90% yield as a viscous yellow oil. $^1$H NMR (300 MHz, CDCl$_3$) δ 0.98 (t, J=7.2 Hz, 6H), 3.04 (q, J=7.2 Hz, 4H), 5.74 (s, 2H), 7.44–8.02 (m, 7H); $^{13}$C NMR (100 MHz, CDCl$_3$) δ 11:34, 48.59, 73.94, 123.52, 125.02, 125.84, 126.52, 127.71, 128.52, 129.49, 131.06, 131.43, 133.60; FABMS m/z 296 (M+Na, 100%); UV-VIS (ACN) λ$_{max}$ 222 nm & 281 nm (ε$_{300\,nm}$=1839 M$^{-1}$cm$^{-1}$).

Example 14

This example describes the characteristics of O$^2$-(3-(1-naphthyl)-E-2-propenyl))-1-(N,N-diethylamino)-diazenen-1-ium-1,2-diolate (having the backbone of compound 6, where n=1, Y=H, R$_1$–R$_7$=H, X=diethylamino).

30% yield as light yellow solid mp 65–67° C., $^1$H NMR (300 MHz, CDCl$_3$) δ 1.07–1.13 (t, J=7 Hz, 6H), 3.07–3.14 (q, J=7 Hz, 4H), 5.03–5.18 (d, J=7 Hz, 1H), 6.37–6.44 (m, 1H), 7.43–7.51 (m, 4H), 7.57–7.59 (d, J=7 Hz, 1H), 7.77–7.80 (d, J=7 Hz, 1H), 7.82–7.85 (d, J=7 Hz, 1H), 8.08–8.18 (d, J=15 Hz, 1H); $^{13}$C NMR (100 MHz, CDCl$_3$) δ 11.65, 48.81, 74.48, 123.70, 124.20, 125.57, 125.88, 126.26, 128.54, 131.09, 132.50, 133.55, and 133.81; FAB Mass m/z 322 (M+Na, 47%). UV-VIS: λ$_{max}$ 298 nm (ε=8500 M$^{-1}$cm$^{-1}$) in 99.1/0.1% water/ACN.

Example 15

This example describes the characteristics of O$^2$-(3-(5,8-dimethoxy-1-naphthyl)-E-2-propenyl)-1-(N,N-diethylamino)-diazenen-1-ium-1,2-diolate (having the backbone of compound 6, where n=1, Y=H, R$_1$–R$_3$, R$_5$–R$_6$=H, R$_4$=R$_7$=MeO, X=diethylamino).

5% yield as viscous yellow oil, $^1$H NMR (300 MHz, CDCl$_3$) δ 1.0–1.04 (t, J=7 Hz, 6H), 2.98–3.05 (q, J=7 Hz, 4H), 3.78 (s, 3H), 3.84 (s, 3H), 4.88–4.90 (d, J=7 Hz, 1H), 5.90–6.0 (m, 1H), 6.61–6.69 (m, 2H), 7.30–7.39 (m, 2H), 7.8–7.85 (d, J=16 Hz, 1H), 8.12–8.15 (d, J=7 Hz, 1H); $^{13}$C NMR (100 MHz, CDCl$_3$) δ 11.81, 49.01, 55.97, 56.48, 75.10, 103.67, 106.36, 122.59, 124.47, 125.63, 127.33, 127.42, 134.61, 140.06, 149.94, and 151.4; FAB Mass m/z 382 (M+Na, 34%); UV-VIS λ$_{max}$ 336 nm (ε=9780 M$^{-1}$cm$^{-1}$) in 99.1/0.1% water/ACN.

Example 16

This example describes the characteristics of O$^2$-(5,8-dimethoxy-1-naphthylmethyl)-1-(N,N-diethylamino)-diazen-1-ium-1,2-diolate (having the backbone of compound 6, where n=0, Y=H, R$_1$–R$_3$, R$_5$–R$_6$=H, R$_4$=R$_7$=MeO, X=diethylamino).

36% yield as a light yellow solid. mp 71–73° C., $^1$H NMR (300 MHz, CDCl$_3$) δ 1.05 (t, J=7.2 Hz, 6H), 3.09 (q, J=7.2 Hz, 4H), 3.90 (s, 3H), 3.95 (s, 3H), 6.04 (s, 2H), 6.74 (s, 2H), 7.40–7.56 (m, 2H), 8.21 (d, J=8.3 Hz, 1H); $^{13}$C NMR (100 MHz, CDCl$_3$) δ 11.29, 48.45, 55.36, 55.38, 75.66, 103.20, 104.88, 121.80, 123.67, 124.84, 125.41, 127.12, 131.84, 149.29, 150.64; FABMS m/z 356 (M+Na, 100%); UV-VIS (ACN) $\lambda_{max}$ 245 nm & 323 nm ($\epsilon_{350\ nm}$=1510 M$^{-1}$cm$^{-1}$).

Example 17

This example describes the characteristics of O$^2$-(5,8-dimethoxy-2-naphthylmethyl)-1-(N,N-diethylamino)-diazen-1-ium-1,2-diolate (having the backbone of compound 9, where n=0, Y=H, R$_1$–R$_3$, R$_5$–R$_6$=H, R$_4$=R$_7$=MeO, X=diethylamino).

25% yield as viscous yellow oil. $^1$H NMR (300 MHz, CDCl$_3$) δ 0.99 (t, J=7.1 Hz, 6H), 3.04 (q, J=7.1 Hz, 4H), 3.93 (bs, 6H), 5.43 (s, 2H), 6.69 (s, 2H), 7.52 (dd, J=8.6 Hz & 1.8 Hz, 1H), 8.16–8.22 (m, 2H); $^{13}$C NMR (100 MHz, CDCl$_3$) δ 11.46, 48.73, 55.61, 55.68, 75.98, 103.53, 103.64, 121.91, 122.28, 125.80, 126.03, 126.09, 133.15, 149.32, 149.54; FABMS m/z 356 (M+Na, 100%); UV-VIS (ACN) $\lambda_{max}$ 248 nm & 322 nm ($\epsilon_{350\ nm}$=1498 M$^{-1}$cm$^{-1}$).

Example 18

This example describes the characteristics of O$^2$-(3-methoxy-2-naphthylmethyl)-1-(N,N-diethylamino)-diazen-1-ium-1,2-diolate (having the backbone of compound 9, where n=0, Y=H, R$_1$, R$_3$, R$_4$–R$_7$=H, R$_2$=MeO, X=diethylamino).

72% yield as a viscous yellow oil. $^1$H NMR (300 MHz, CDCl$_3$) δ 1.03 (t, J=7.2 Hz, 6H), 3.09 (q, J=7.2 Hz, 4H), 3.94 (s, 3H), 5.50 (s, 2H), 7.11 (s, 1H), 7.30–7.44 (m, 2H), 7.71–7.75 (m, 2H); $^{13}$C NMR (100 MHz, CDCl$_3$) δ 11.29, 48.47, 55.11, 71.00, 104.86, 123.58, 125.55, 126.17, 126.31, 127.48, 128.10, 128.39, 128.44, 134.22, 155.20; FABMS m/z 326 (M+Na, 100%); UV-VIS (ACN) $\lambda_{max}$ 227 nm, 273 nm & 327 nm ($\epsilon$ 300 nm=1255 M$^{-1}$cm$^{-1}$).

Example 19

This example describes the characteristics of O$^2$-(3-(3-methoxy-2-naphthyl)-E-2-propenyl)-1-(N,N-diethylamino)-diazen-1-ium-1,2-diolate (having the backbone of compound 9, where n=1, Y=H, R$_1$, R$_3$, R$_4$–R$_7$=H, R$_2$=MeO, X=diethylamino).

35% yield as viscous yellow oil. $^1$H NMR (300 MHz, CDCl$_3$) δ 1.09–1.4 (t, J=7 Hz, 6H), 3.08–3.15 (q, 4H), 3.95 (s, 3H), 4.96–4.99 (d, J=7 Hz, 2H), 6.53–6.59 (s, 1H), 7.10 (s, 1H), 7.10–7.15 (d, J=16 Hz, 1H), 7.32–7.35 (m, 1H), 7.39–7.42 (m, 1H), 7.69–7.73 (d, J=7 Hz, 1H), 7.73–7.76 (d, J=7 Hz, 1H), 7.85 (s, 1H); $^{13}$C NMR (100 MHz, CDCl$_3$) δ 11.78, 49.01, 55.54, 105.45, 124.08, 124.96, 126.48, 126.66, 127.07, 127.93, 128.74, 130.97, 134.43, and 155.70; FAB Mass m/z 352 (M+Na, 100%). UV-VIS: $\lambda_{max}$ 297 nm ($\epsilon$=6360 M$^{-1}$cm$^{-1}$) in 99.1/0.1% water/ACN.

Example 20

This example describes the characteristics of O$^2$-(3-(3-methoxy-2-naphthyl)-E-2-propenyl)-1-(piperidin-1-yl)-diazenen-1-ium-1,2-diolate (having the backbone of compound 9 described below), where n=1, Y=H, R$_1$, R$_3$, R$_4$–R$_7$=H, R$_2$=MeO, X=piperidyl).

20% yield viscous yellow oil. $^1$H NMR (300 MHz, CDCl$_3$) δ 1.5–1.6 (m, 2H), 1.73–1.8 (m, 4H), 3.46–3.83 (t, J=7 Hz, 4H), 3.96 (s, 3H), 4.91–4.94 (d, J=7 Hz, 2H), 6.53–6.58 (m, 1H), 7.08 (s, 1H), 7.08–7.11 (d, J=16 Hz, 1H), 7.32–7.35 (m, 1H), 7.38–7.42 (m, 1H), 7.71–7.74 (d, J=7 Hz, 1H), 7.69–7.74 (d, J=7 Hz, 1H), 7.78 (s, 1H); $^{13}$C NMR (100 MHz, CDCl$_3$) δ 23.59, 24.98, 53.09, 74.96, 105.50, 124.12, 125.25, 126.51, 126.67, 127.05, 127.13, 127.96, 128.78, 130.76, 134.45, and 155.69; FAB Mass m/z 364 (M+Na, 74%) UV-VIS $\lambda_{max}$ 251 & 306 nm in 99.1/0.1% water/ACN.

Example 21

This example describes the characteristics of O$^2$-(4-methyl-1-naphthylmethyl)-1-(N,N-diethylamino)-diazen-1-ium-1,2-diolate (having the backbone of compound 6, where n=0, Y=H, R$_1$–R$_2$, R$_4$–R$_7$=H, R$_3$=Me, X=diethylamino).

25% yield as clear viscous oil. $^1$H NMR (300 MHz, CDCl$_3$) δ 0.96 (t, J=7.2 Hz, 6H), 2.68 (s, 3H), 3.05 (q, J=7.2 Hz, 4H), 4.97 (s, 2H), 7.44 (d, J=7.2 Hz, 2H), 7.53–7.56 (m, 2H), 8.03 (d, J=6.3 Hz, 1H), 8.10 (d, J=6.3 Hz, 1H); $^{13}$C NMR (100 MHz, CDCl$_3$) δ 11.44, 19.62, 48.67, 74.24, 124.19, 124.68, 125.73, 125.83, 126.21, 127.77, 129.30, 131.61, 132.84, 136.00; FABMS m/z 310 (M+Na, 100%); UV-VIS (ACN) $\lambda_{max}$ 226 nm & 287 nm ($\epsilon_{300\ nm}$=6423 M$^{-1}$cm$^{-1}$).

Example 22

This example describes the characteristics of O$^2$-(2,3-dimethoxy-1-naphthylmethyl)-1-(N,N-diethylamino)-diazen-1-ium-1,2-diolate (having the backbone of compound 6, where n=0, Y=H, R$_3$–R$_7$=H, R$_1$–R$_2$=OMe, X=diethylamino).

50% yield as viscous yellow oil. $^1$H NMR (300 MHz, CDCl$_3$) δ 0.98 (t, J=7.1 Hz, 6H), 3.04 (q, J=7.1 Hz, 4H), 3.97 (s, 3H), 3.99 (s, 3H), 5.81 (s, 2H), 7.19 (s, 1H), 7.36–7.42 (m, 2H), 7.66–7.72 (m, 1H), 8.00–8.05 (m, 1H); $^{13}$C NMR (100 MHz, CDCl$_3$) δ 11.39, 48.50, 55.58, 62.04, 66.85, 108.71, 122.84, 123.82, 124.61, 125.31, 126.88, 127.97, 131.20, 149.31, 151.61; FABMS m/z 356 (M+Na, 85%); UV-VIS (ACN) $\lambda_{max}$ 231 nm, 280 nm & 327 nm ($\epsilon_{300\ nm}$=2615 M$^{-1}$cm$^{-1}$).

Example 23

This example describes a general procedure for the determination of diazeniumdiolate released upon photolysis of compounds 6 and 9. The amiNO-700 probe was calibrated using ascorbic acid/sodium nitrite before and after NO measurements were recorded. Calibration curves were prepared in order to relate current (detected by the instrument) with concentration of NO. Stock solutions of compounds 6 and 9 were prepared to be 100 μM in acetonitrile, and of these 15 μL aliquots were diluted into to 3 mL of a pH 12.2 aqueous solution. The resulting 0.498 μM solutions were photolyzed with a Xenon arc lamp and a long-pass 324 nm filter for lengths of time appropriate to reach 100% conversion (6–7 minutes for most compounds at this concentration). Under these basic conditions any diazeniumdiolate generated photochemically is stable, and neither sodium-1-(N,N-diethylamino)-1-diazen-1-ium-1,2-diolate (compound 1) or sodium-1-(piperidin-1-yl)-diazen-1-ium-1,2-diolate (compound 20) absorbs at wavelengths above 324 nm. No NO was measured electrochemically at this pH, indicating there are no photochemical paths that lead directly to NO. The NO associated with the photochemically generated diazeniumdiolate was liberated by the addition of 10 μL of 1.0 M sulfuric acid (final solution pH's were typically 2–3. Using the calibration curve and the fact that the amount of NO released upon thermal decomposition of compounds 1 and 20 was calculated to be 1.5 and 1.8 eq. respectively, the absolute percentage of diazeniumdiolate generated upon photolysis of compounds 6 and 9 was determined. FIG. 2 depicts the amount of nitric oxide produced upon photolysis from a selection of 1-methylnaphthyl and 2-methylnaphthyl-$O^2$-substituted diazeniumdiolates having a backbone of compounds 6 and 9. After photolysis (t=0 sec) there is no nitric oxide production, it is only liberated upon acidification of the solution (t=50 sec) indicating that all the nitric oxide is derived from the photochemically liberated diazeniumdiolate compound 1.

Example 24

This example describes the general procedure for the determination of the rate of NO release from compounds 6 and 9 upon photolysis. Stock solutions of compounds 6 and 9 were prepared to be 100 μM in acetonitrile, and of these 15 μL aliquots were diluted into to 3 μL of aqueous solutions at the appropriate pH (10 mM phosphate and acetate buffers). The probe was allowed to equilibrate in the sample solution before 10 seconds of photolysis using a Xenon arc lamp with a long-pass 324 nm filter. The rate of NO release was then monitored over the appropriate time span. For comparison, the thermal decay of both compounds 1 and 20 were recorded under the same conditions as those of the photochemical experiments. The rate of photochemical release of NO was shown to match the rate of thermal decomposition in all cases.

Figure 3:
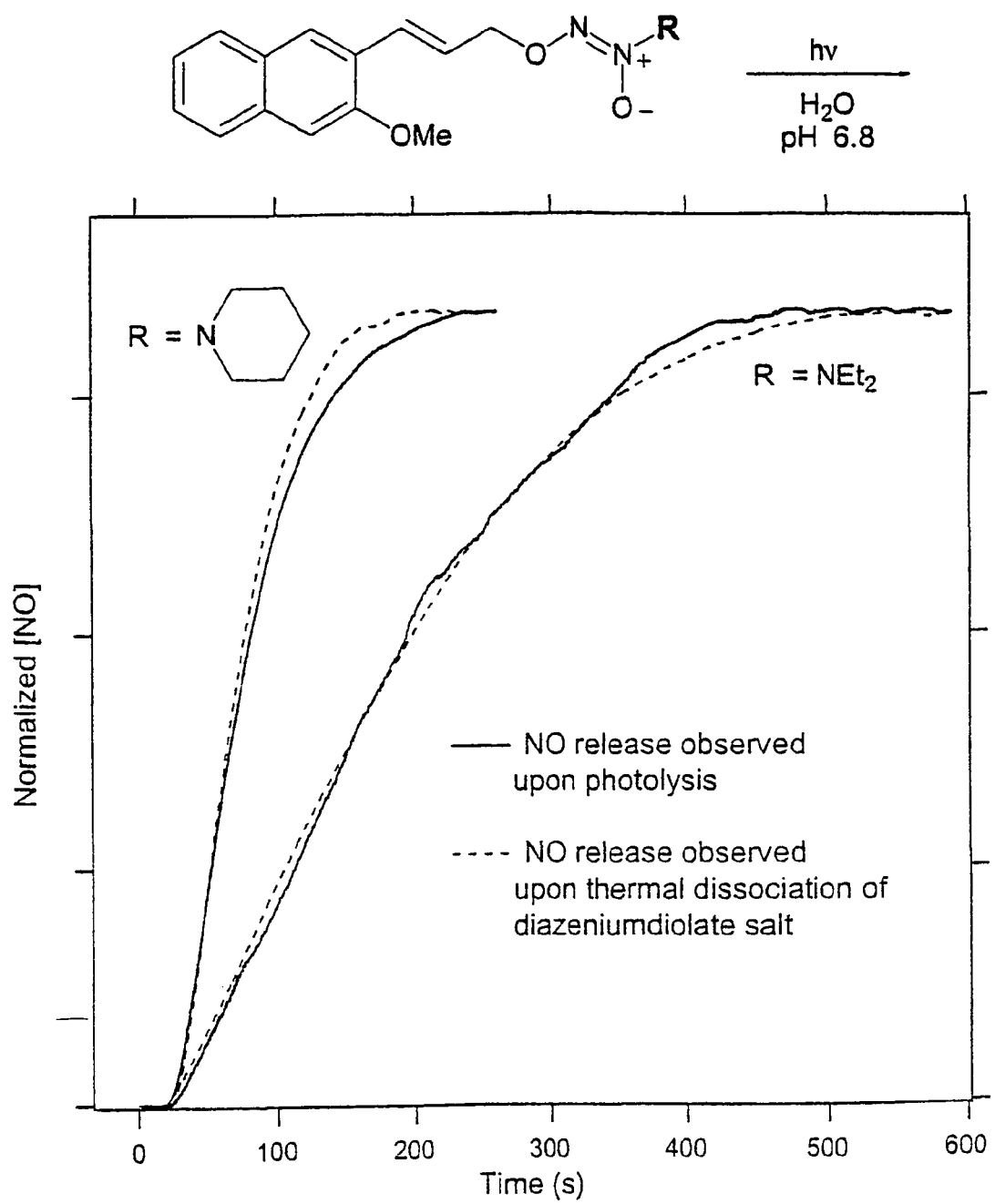
FIG. 3 is a graph showing the decay of diazeniumdiolate compounds 1 and 20 upon photolysis of selected compounds from 6 and 9.

FIG. 3 shows the decay of diazeniumdiolate compounds 1 and 20 upon photolysis of $O^2$-(3-(3-methoxy-2-naphthyl)-E-2-propenyl)-1-(diethylamino)-diazen-1-ium-1,2-diolate (having the backbone of compound 9 described below), where n=1, Y=H, $R_1$, $R_3$, $R_4$–$R_7$=H, $R_2$=MeO, X=diethylamino) and $O^2$-(3-(3-methoxy-2-naphthyl)-E-2-propenyl)-1-(piperidin-1-yl)-diazenen-1-ium-1,2-diolate (having the backbone of compound 9 described below), where n=1, Y=H, $R_1$, $R_3$, $R_4$–$R_7$=H, $R_2$=MeO, X=piperidyl). The decay to nitric oxide and amine occurs at a rate consistent with the known thermal decays of these diazemiumdiolates.

Example 25

Compounds 6 and 9 are soluble in 99% aqueous acetonitrile up to 20 μM and are thermally stable indefinitely at pH 4–11, 25° C. at this concentration. Analysis of the products following photolysis (Rayonet, 300 or 350 nm, Xenon arc lamp with a long-pass 324 nm filter) of compounds 6 and 9 in both argon- and oxygen-saturated 99% aqueous acetonitrile is summarized in Table 2 below. Quantification of NO released upon photolysis was performed electrochemically with an inNO Nitric Oxide Measuring System using an ami-700 probe (Innovative Instruments Inc., Tampa, Fla.).

TABLE 2

Quantum yields and diazeniumdiolate/NO release from compounds 6 and 9.

| Reactant | —X | Quantum Yield[a,b] | % Diazeniumdiolate | % NO |
|---|---|---|---|---|
| 6 (n = 0, Y = $R_1$–$R_7$ = H) | —$NEt_2$ | 0.01[a] | 1 | 1.5 |
| 6 (n = 1, Y = $R_1$–$R_7$ = H) | —$NEt_2$ | 0.12[a] | 25 | 37.5 |
| 6 (n = 0, Y = $R_1$–$R_3$, $R_5$–$R_6$ = H, $R_4$, $R_7$ = OMe) | —$NEt_2$ | 0.12[b] | 40 | 60 |
| 6 (n = 1, Y = $R_1$–$R_3$, $R_5$–$R_6$ = H, $R_4$, $R_7$ = OMe) | —$NEt_2$ | 0.66[b] | 95 | 143 |
| 9 (n = 0, Y = $R_1$–$R_3$, $R_5$–$R_6$ = H, $R_4$, $R_7$ = OMe) | —$NEt_2$ | 0.05[b] | 34 | 51 |
| 9 (n = 0, Y = $R_1$, $R_3$–$R_7$ = H, $R_2$ = OMe) | —$NEt_2$ | 0.02[a] | 20 | 30 |
| 9 (n = 1, Y = $R_1$, $R_3$–$R_7$ = H, $R_2$ = OMe) | —$NEt_2$ | 0.15[b] | 50 | 75 |
| 9 (n = 1, Y = $R_1$, $R_3$–$R_7$ = H, $R_2$ = OMe) | pipridyl | 0.10[b] | 50 | 90 |

[a,b]Photolysis were carried out at a concentration of ~20 μM in 90–95% aqueous acetonitrile at 300 nm (rayonet reactor)[a] and 355 nm (ND: YAG LASER)[b] in a quartz/Pyrex cell. Samples were irradiated for below 40% conversion.
NO measurements were carried using an inNO 700 probe (Innovative Instruments, Tampa, Florida), 0.498 μM solutions were photolyzed with a Xenon arc lamp and a long-pass 324 nm filter for lengths of time appropriate to reach 100% conversion.

Example 26

Substitution of 1-naphthol's in the 5 and 8 position with electron withdrawing substituents results in enhanced photoacidity, similarly the photoacidity of 2-naphthol's is significantly enhanced by substitution in the 3, 5 and 8-positions. Based on this literature, we prepared the following series of $O^2$-substituted diazeniumdiolates compounds 6 and 9 and have examined the effect of electron-donating substituents on the observed photochemistry and on the efficiency of NO release.

Several trends have emerged from this study. Use of the allylnaphthyl protecting group (compound 6 where n=1, Y=H, $R_1$–$R_7$=H, X=diethylamino) gave significant uncaging of compound 1 (25%) upon photolysis at >324 nm. Substitution of the 2-methylnaphthyl system with a methoxy group in the 3 position (compound 9 where n=0, Y=H, $R_1$, $R_3$–$R_7$=H, $R_2$=MeO, X=diethylamino) also saw a significant rise in the amount of diazeniumdiolate released upon photolysis (20%) relative to the unsubstituted analog. These two effects were shown to be somewhat cumulative, in that photolysis of compound 9 (where n=1, Y=H, $R_1$, $R_3$–$R_7$=H, $R_2$=MeO, X=diethylamino) and compound 9 (where n=0, Y=$R_1$, $R_3$–$R_7$=H, $R_2$=OMe, X=diethylamino) both gave 50% of the desired pathway.

Since the acidity of 2-naphthol's in the excited state is enhanced by substitution with electron withdrawing groups in the 3, 5 and 8 positions, we studied the $O^2$-(5,8-dimethoxy-2-naphthylmethyl)-1-(N,N-diethylamino)-diazen-1-ium-1,2-diolate (compound 9 where n=0, Y=H, $R_1$–$R_3$, $R_5$–$R_6$=H, $R_4$–$R_7$=MeO, X=diethylamino). The trend between photoheterolytic cleavage of the C—O bond and excited state acidities of the corresponding naphtol was borne out and 34% compound 1 was observed upon photolysis of this compound in aqueous solution. Photolysis of 5,8-dimethoxy-1-methylnaphthyl diazeniumdiolate (compound 6 where n=0, Y=H, $R_1$–$R_3$, $R_5$–$R_6$=H, $R_4$, $R_7$=MeO, X=diethylamino) resulted in similar amounts of NO release (40%) and this study culminated in the photolysis of $O^2$-(3-(5,8-dimethoxy-1-naphthyl)-E-2-propenyl)-1-(N,N-diethylamino)-diazenen-1-ium-1,2-diolate (compound 6 where n=1, Y=H, $R_1$–$R_3$, $R_5$–$R_6$=H, $R_4$=$R_7$=MeO, X=diethylamino) upon photolysis above 325 nm in aqueous solution results in the highly efficient ($\Phi$=0.66) photochemical release of compound 1 in near quantitative yield ~95%), while none of the genotoxic nitrosamines compound 12 are formed.

Example 27

Figure 4:
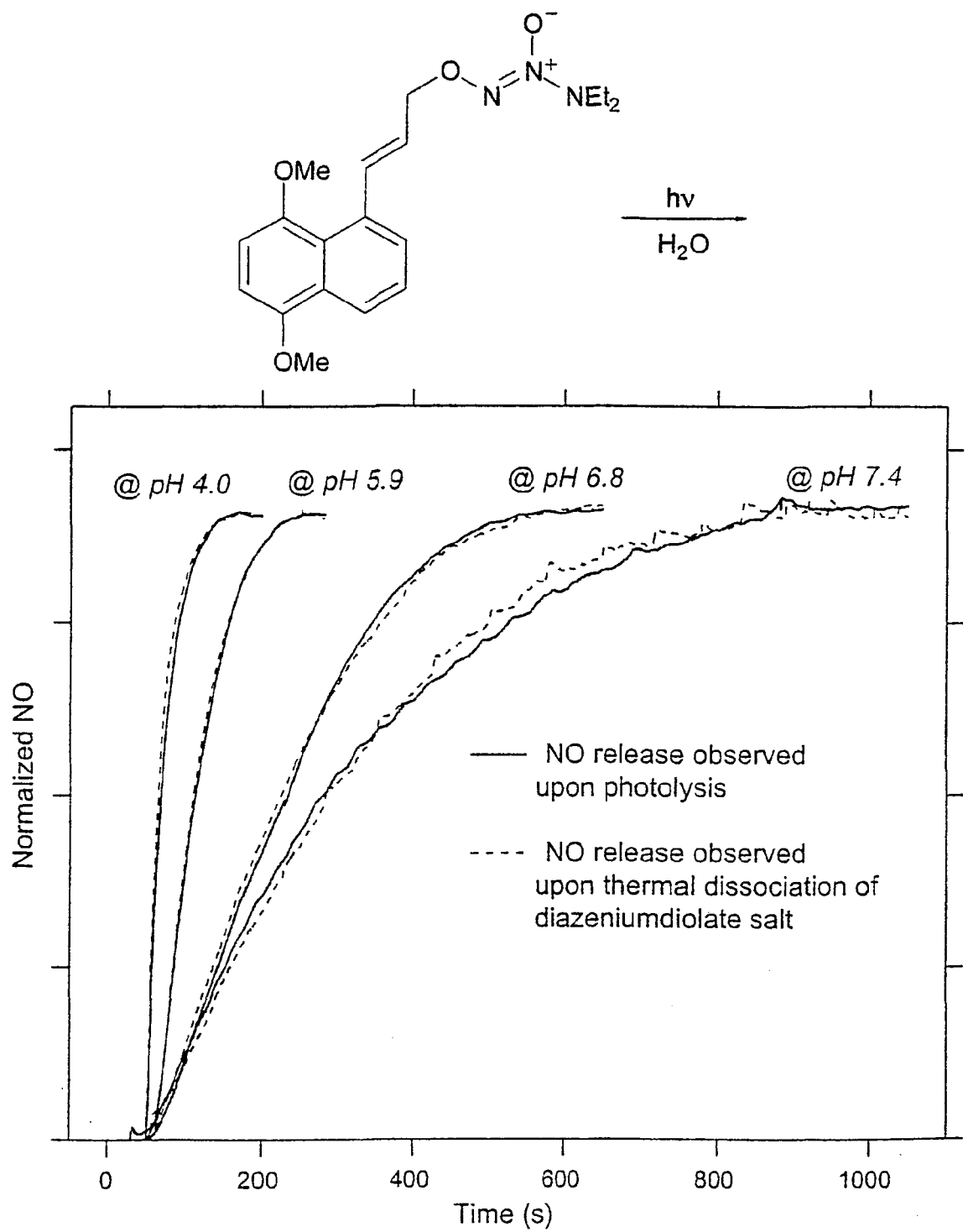
FIG. 4 is a ¹H NMR analysis of the products observed following photolysis of compound 1.

FIG. 4 describes direct evidence for the photochemical generation of sodium-1-(N,N-diethylamino)-diazen-1-ium-1,2-diolate compound 1 upon photolysis. The diazeniumdiolate was detected using proton nuclear magnetic resonance ($^1$H NMR) and its presence after photolysis was determined unequivocally by comparing the result with a sample spiked with a control sample of 1 (shown in (b)).

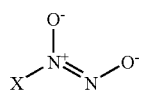

1

Example 28

Figure 5:
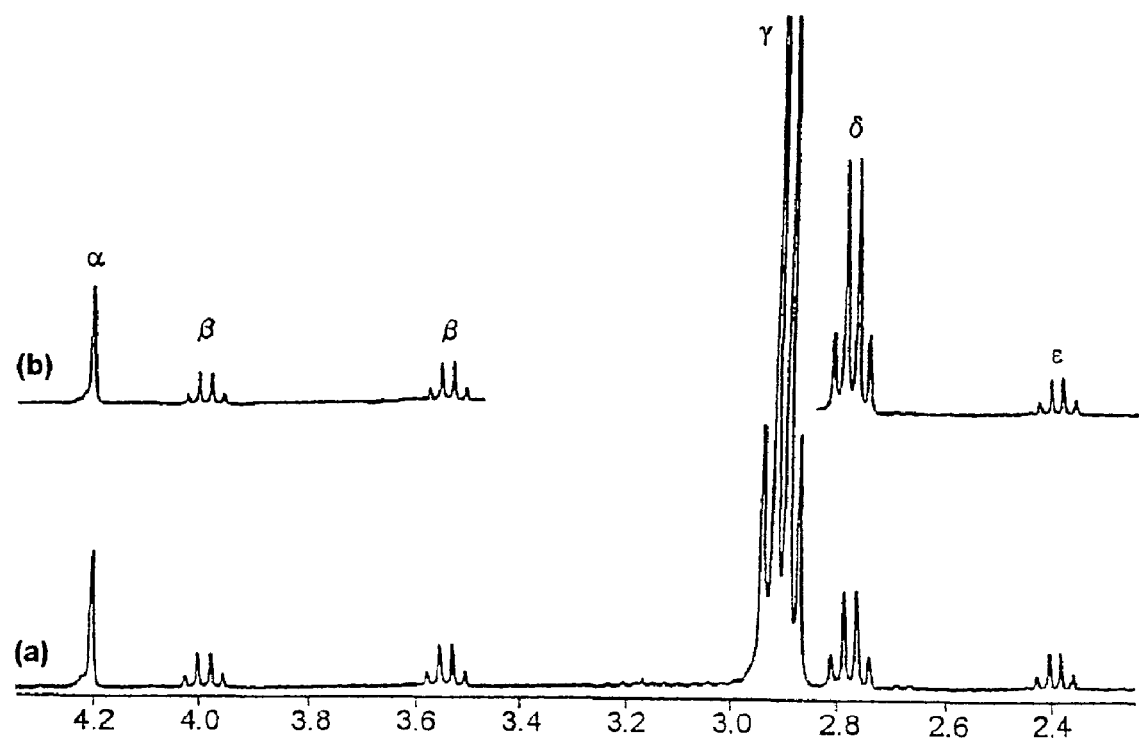
FIG. 5 is a graph which shows that the rate of release of nitric oxide from the photochemically generated diazeniumdiolate compound 1 is pH dependent.

FIG. 5 is a graph which shows that the rate of release of nitric oxide from the photochemically generated diazeniumdiolate compound 1 is pH dependent. As shown, this pH dependence follows the same pH dependence for the release from authentic samples of diazeniumdiolate 1.

The above-described compounds may be targeted to a specific site in a body, and/or may be used for both research and/or biological treatment applications. As one example, not meant to be limiting, any one of the above compounds could be directed to a target site in a body such as a tumor. Once at the desired site, the compounds may be triggered to release NO upon exposure to light. The released NO may help to destroy the tumor in a specifically controlled manner, or the released NO may interact with another biological effector to help mediate a biological process in a controlled manner.

The compounds may also be injected into a mammal and allowed to diffuse naturally throughout the body to a target site where they could be exposed to light to release NO and induce an effect.

It is known that NO acts as a neurotransmitter. It is contemplated that NO-releasing compounds such as compounds 3–11 described herein may also be used as neurotransmitters, or may mediate neuronal effects.

For research purposes, the above-described compounds may find utility in experimental situations where it is necessary to know the precise moment of NO release and also control the rate of NO release.

It is known that NO prevents aggregation of platelets in long-term storage. As one example not meant to be limiting, the NO-releasing compound may be added to the stored platelets in an amount effective to prevent platelet aggregation. The platelets and the compound may then be irradiated at a wavelength sufficient to release NO but not an amount that would substantially destroy the biological activity of the platelets.

In another embodiment, the above-described compounds may be used in a method to pathogen inactivate a fluid containing blood or blood products. The blood products to be pathogen inactivated include but are not limited to red blood cells, white blood cells, platelets and plasma. Any of the above-described compounds may be added to a bag or container (not shown) containing the fluid to be pathogen inactivated, or may be added to a bag before the addition of the fluid to be pathogen inactivated. The compound may then be exposed to light of a desired wavelength to release NO into the fluid. Any of the above-described compounds may be used, either alone or in combination with other above-described compounds. A photosensitizer may also be added either before or after the addition of the fluid to be pathogen inactivated, or before or after the NO-releasing compound. Any photosensitizer known in the art may be used. The fluid to be pathogen inactivated, the NO-releasing compound and the photosensitizer may then be irradiated at a wavelength sufficient to inactivate any pathogens contained in the fluid as well as releasing NO into the fluid.

NO by itself is known to kill certain pathogens. It is further contemplated that NO-releasing compounds themselves may be used to inactivate pathogens without the presence of a photosensitizer.

Although the description above contains many specificities, these should not be construed as limiting the scope of the invention, but as merely providing illustrations of some of the embodiments of this invention. Various changes and modifications to the embodiments described herein will be apparent to those skilled in the art. Such changes and modifications can be made without departing from the spirit and scope of the present invention and without diminishing its attendant advantages.

The invention claimed is:

1. A compound having any one of the following structures:

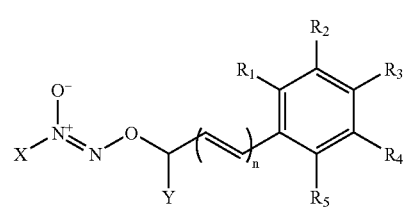

3

-continued

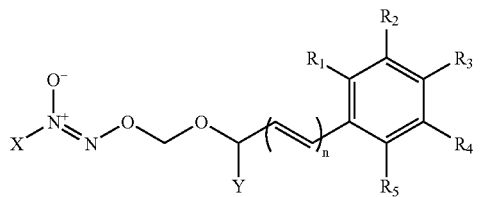

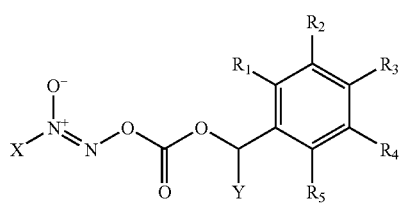

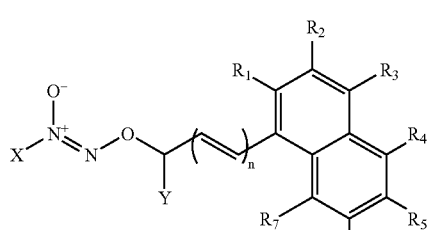

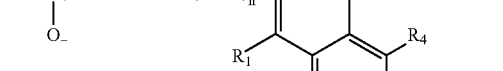

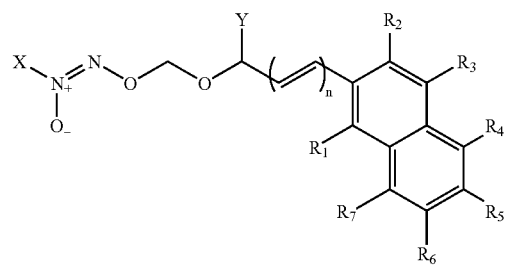

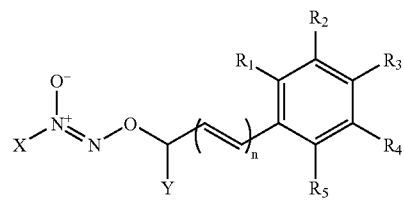

n = 0, 1 wherein:

X=—NR¹R², where R¹ and R² are selected from the group consisting of —H, —C₁ through —C₁₂ alkyl, phenyl, substituted phenyl, —R'NH₂, and —R'—NH—R", where R' and R" are alkyl groups including straight chain and branched groups, as well as cycloalkyl, and where X may also equal prolinyl, imidizoyl, pyrrolyl, or pyridyl, where these groups are bonded at N;

Y=—H, —C₁ through —C₁₂ alkyl, phenyl, substituted phenyl, —OR', or —NR'R", where R' and R" are alkyl groups including straight chain and branched groups, as well as cycloalkyl; and R₁–R₇=—H, —C₁ through —C₁₂ alkyl, phenyl, substituted phenyl, —OH, —OR', —O(CH₂CH₂O)ₙH, where n=1–12, —NH₂, —NR'R", —SH, —SR', —R'CO₂H, —R'CO₂R", —OR'CO₂H, —OR'CO₂R", C(O)H, C(O)R¹, or CH₂OH, where R' and R" are alkyl groups including straight chain and branched groups, as well as cycloalkyl, and where R₁–R₇ may also equal any sugar or carbohydrate where this group is bonded at O.

2. A method for temporally releasing NO from a compound having any one of the following structures:

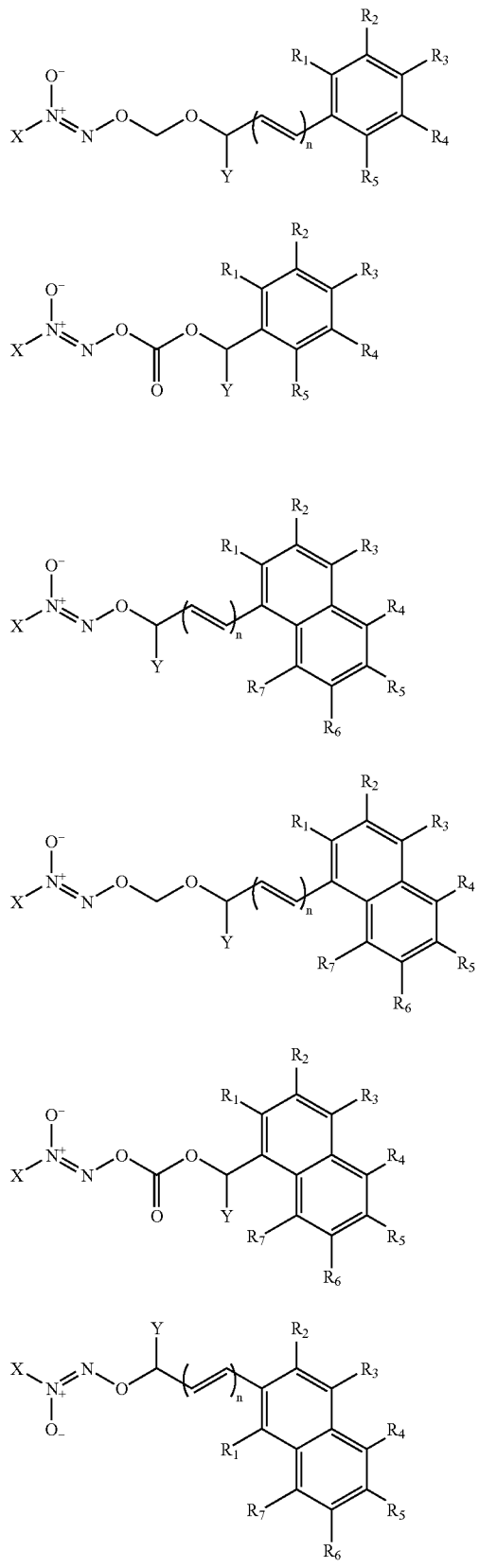

n = 0, 1 wherein:
X=—NR¹R², where R¹ and R² are selected from the group consisting of —H, —C₁ through —C₁₂ alkyl, phenyl, substituted phenyl, —R'NH₂, and —R'—NH—R", where R' and R" are alkyl groups including straight chain and branched groups, as well as cycloalkyl, and where X may also equal prolinyl, imidizoyl, pyrrolyl, or pyridyl, where these groups are bonded at N;

Y=—H, —C₁ through —C₁₂ alkyl, phenyl, substituted phenyl, —OR', or —NR'R", where R' and R" are alkyl groups including straight chain and branched groups, as well as cycloalkyl;

R₁–R₇=—H, —C₁ through —C₁₂ alkyl, phenyl, substituted phenyl, —OH, —OR', —O(CH₂CH₂O)ₙH, where n=1–12, —NH₂, —NR'R", —SH, —SR', —R'CO₂H, —R'CO₂R", —OR'CO₂H, —OR'CO₂R", C(O)H, C(O)R¹, or CH₂OH, where R' and R" are alkyl groups including straight chain and branched groups, as well as cycloalkyl, and where R₁–R₇ may also equal any sugar or carbohydrate where this group is bonded at O; and comprising the steps of;
exposing the compound to light of a wavelength sufficient to release NO from the compound; and
releasing the NO from the compound.

3. The method of claim 2 wherein the wavelength sufficient to release NO from the compound is between 250–700 nm.

4. A method of administering nitric oxide to cells comprising administering to the cells an effective amount of a nitric oxide releasing prodrug including any one of the following structures:

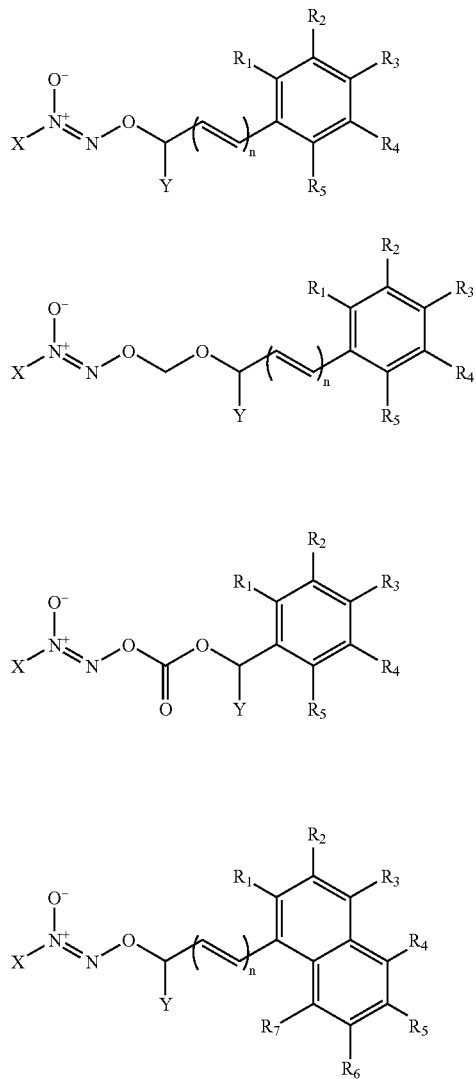
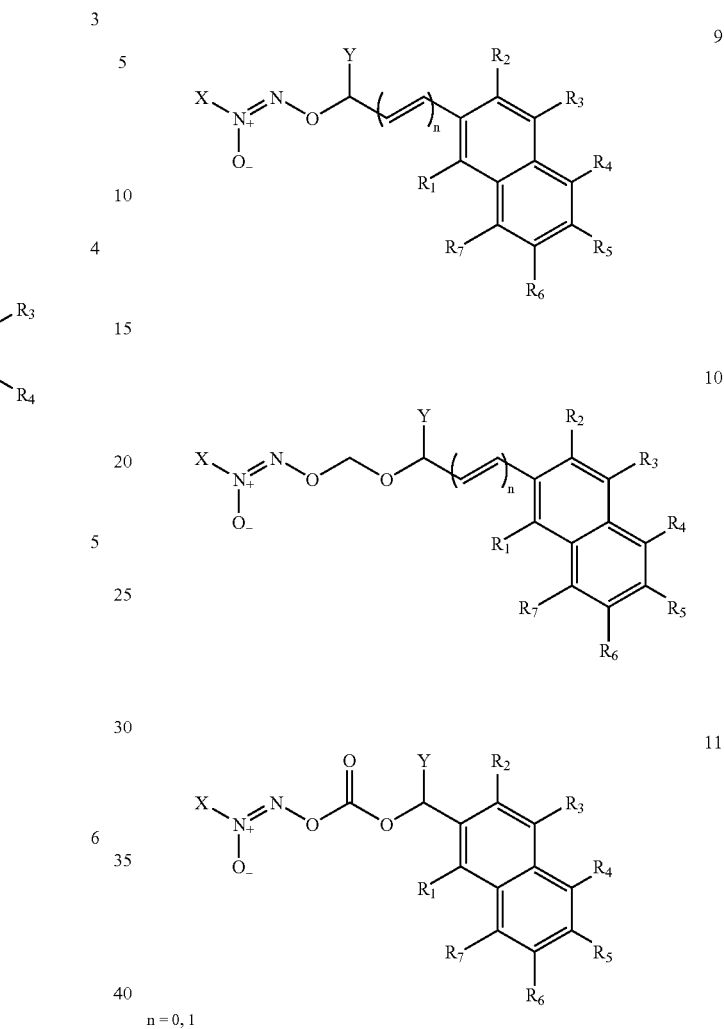

n = 0, 1 wherein:

X=—NR¹R², where R¹ and R² are selected from the group consisting of —H, —$C_1$ through —$C_{12}$ alkyl, phenyl, substituted phenyl, —R'NH₂, and —R'—NH—R", where R' and R" are alkyl groups including straight chain and branched groups, as well as cycloalkyl, and where X may also equal prolinyl, imidizoyl, pyrrolyl, or pyridyl, where these groups are bonded at N;

Y=—H, —$C_1$ through —$C_{12}$ alkyl, phenyl, substituted phenyl, —OR', or —NR'R", where R' and R" are alkyl groups including straight chain and branched groups, as well as cycloalkyl;

$R_1$–$R_7$=—H, —$C_1$ through —$C_{12}$ alkyl, phenyl, substituted-phenyl, —OH, —OR', —O($CH_2CH_2O)_n$H, where n=1–12, —NH₂, —NR'R", —SH, —SR', —R'CO₂H, —R'CO₂R", —OR'CO₂H, —OR'CO₂R", C(O)H, C(O)R¹, or CH₂OH, where R' and R" are alkyl groups including straight chain and branched groups, as well as cycloalkyl, and where $R_1$–$R_7$ may also equal any sugar or carbohydrate where this group is bonded at O; and a pharmaceutically acceptable carrier;

the method comprising the steps of;

administering to the cells an effective amount of any one or more NO releasing prodrugs; and irradiating the compound with light of an appropriate wavelength to release NO.

5. The method of claim 4 wherein the NO releasing prodrug is administered to the cells topically.

6. The method of claim 4 wherein the NO releasing prodrug is administered to the cells by injection.

7. The method of claim 4 wherein the NO releasing prodrug is administered to the cells by being suspended into aqueous media.

8. The method of claim 4 wherein the cells are stored platelets.

9. A method for the pathogen inactivation of blood or a blood product comprising the steps of:

adding to the blood or blood product an effective amount of any one or more of the following structures:

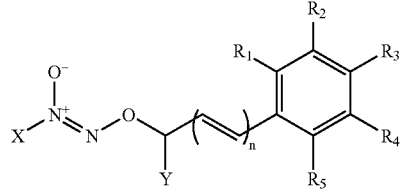

3

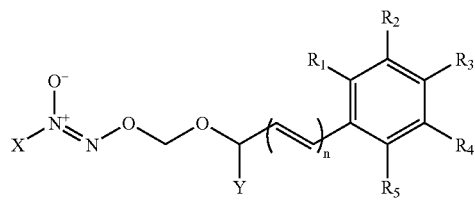

4

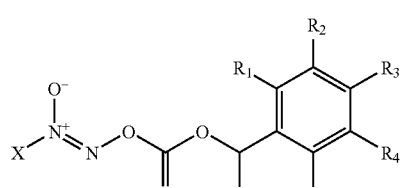

5

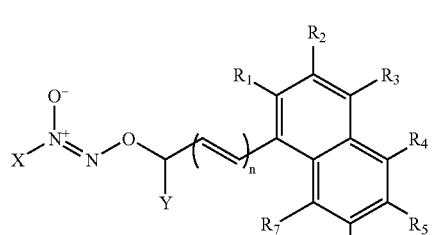

6

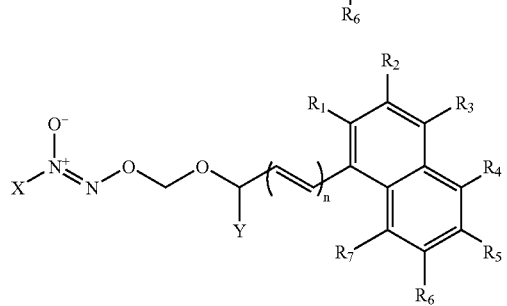

7

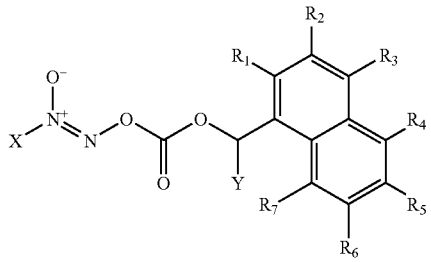

8

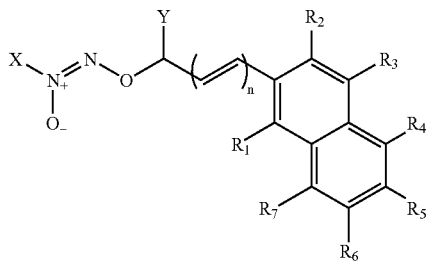

9

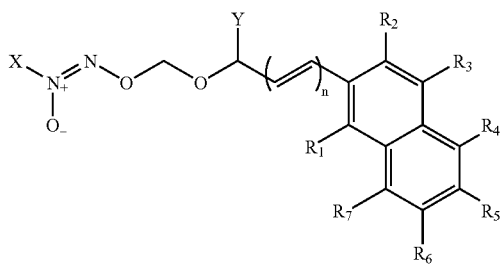

10

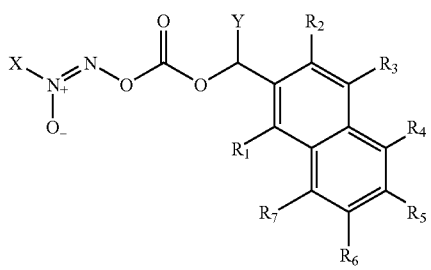

11 n = 0, 1 wherein:

X=—NR$^1$R$^2$, where R$^1$ and R$^2$ are selected from the group consisting of —H, —C$_1$ through —C$_{12}$ alkyl, phenyl, substituted phenyl, —R'NH$_2$, and —R'—NH—R", where R' and R" are alkyl groups including straight chain and branched groups, as well as cycloalkcyl, and where X may also equal prolinyl, imidizoyl, pyrrolyl, or pyridyl, where these groups are bonded at N;

Y=—H, —C$_1$ through —C$_{12}$ alkyl, phenyl, substituted phenyl, —OR', or —NR'R", where R' and R" are alkyl groups including straight chain and branched groups, as well as cycloalkyl;

R$_1$–R$_7$=—H, —C$_1$ through —C$_{12}$ alkyl, phenyl, substituted phenyl, —OH, —OR', —O(CH$_2$CH$_2$O)$_n$H, where n=1–12, —NH$_2$, —NR'R", —SH, —SR', —R'CO$_2$H, —R'CO$_2$R", —OR'CO$_2$H, —OR'CO$_2$R", C(O)H, C(O)R$^1$, or CH$_2$OH, where R' and R" are alkyl groups including straight chain and branched groups, as well as cycloalkyl, and where $R_1$–$R_7$ may also equal any sugar or carbohydrate where this group is bonded at O; and exposing the mixture to light for a time sufficient to release nitric oxide from any one or more of the substituted diazeniumdiolate compounds, and inactivate any pathogens contained in the blood or blood product.

10. A method according to claim 9 further including the step of adding a photosensitizer to the blood or blood product to be pathogen inactivated.

11. A compound having any one of the following structures:

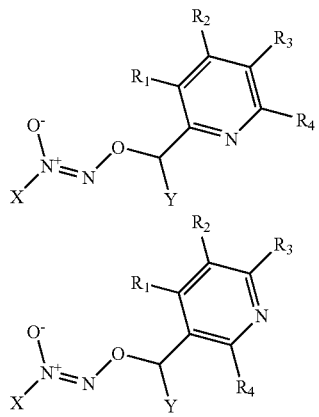

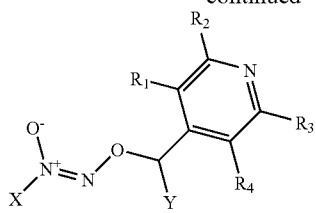

wherein:

$X$=—$NR^1R^2$, where $R^1$ and $R^2$ are selected from the group consisting of —H, —$C_1$ through —$C_{12}$ alkyl, phenyl, substituted phenyl, —R'$NH_2$, and —R'—NH—R", where R' and R" are alkyl groups including straight chain and branched groups, as well as cycloalkyl, and where X may also equal prolinyl, imidizoyl, pyrrolyl, or pyridyl, where these groups are bonded at N;

$Y$=—H, —C, through —$C_{12}$ alkyl, phenyl, substituted phenyl, —OR', or —NR'R", where R' and R" are alkyl groups including straight chain and branched groups, as well as cycloalkyl; and $R_1$–$R_7$=—H, —$C_1$ through —$C_{12}$ alkyl, phenyl, substituted phenyl, —OH, —OR', —O($CH_2CH_2O$)$_n$H, where n=1–12, —$NH_2$, —NR'R", —SH, —SR', —R'$CO_2$H, —R'$CO_2$R", —OR'$CO_2$H, —OR'$CO_2$R", C(O)H, C(O)$R^1$, or $CH_2OH$, where R' and R" are alkyl groups including straight chain and branched groups, as well as cycloalkyl, and where $R_1$–$R_7$ may also equal any sugar or carbohydrate where this group is bonded at O.

* * * * *